US012226400B2

(12) United States Patent
Aizenman et al.

(10) Patent No.: US 12,226,400 B2
(45) Date of Patent: Feb. 18, 2025

(54) NEUROPROTECTIVE DISRUPTION OF KV2.1/SYNTAXIN INTERACTION BY SMALL MOLECULES

(71) Applicant: UNIVERSITY OF PITTSBURGH-OF THE COMMONWEALTH SYSTEM OF HIGHER EDUCATION, Pittsburgh, PA (US)

(72) Inventors: Elias Aizenman, Pittsburgh, PA (US); Carlos Jaime Camacho, Pittsburgh, PA (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 907 days.

(21) Appl. No.: 17/264,982

(22) PCT Filed: Jul. 31, 2019

(86) PCT No.: PCT/US2019/044393
§ 371 (c)(1),
(2) Date: Feb. 1, 2021

(87) PCT Pub. No.: WO2020/028515
PCT Pub. Date: Feb. 6, 2020

(65) Prior Publication Data

US 2021/0322383 A1 Oct. 21, 2021

Related U.S. Application Data

(60) Provisional application No. 62/716,734, filed on Aug. 9, 2018, provisional application No. 62/712,514, filed on Jul. 31, 2018.

(51) Int. Cl.

| | |
|---|---|
| *A61K 31/4155* | (2006.01) |
| *A61K 31/4178* | (2006.01) |
| *A61K 31/428* | (2006.01) |
| *A61K 31/4409* | (2006.01) |
| *A61K 31/506* | (2006.01) |
| *A61K 31/53* | (2006.01) |
| *A61P 25/28* | (2006.01) |

(52) U.S. Cl.
CPC ...... *A61K 31/4155* (2013.01); *A61K 31/4178* (2013.01); *A61K 31/428* (2013.01); *A61K 31/4409* (2013.01); *A61K 31/506* (2013.01); *A61K 31/53* (2013.01); *A61P 25/28* (2018.01)

(58) Field of Classification Search
CPC ............ A61K 31/4155; A61K 31/4178; A61K 31/428; A61K 31/4409; A61K 31/506; A61K 31/53; A61P 25/28
USPC .......................................................... 514/406
See application file for complete search history.

(56) References Cited

U.S. PATENT DOCUMENTS 9,932,382 B2 4/2018 Aizenman et al.
2005/0154230 A1* 7/2005 Yura ...................... A61P 25/04 564/52

FOREIGN PATENT DOCUMENTS

WO WO-2004030664 A2 * 4/2004 ............ A61K 31/17

OTHER PUBLICATIONS

Editorial NN (2018) Focus on neurodegenerative disease. Nature Neuroscience 21(10):1293-1293.
Gribkoff VK & Kaczmarek LK (2017) The need for new approaches in CNS drug discovery: why drugs have failed, and what can be done to improve outcomes. Neuropharmacology 120:11-19.
Uversky VN (2015) Intrinsically disordered proteins and their (disordered) proteomes in neurodegenerative disorders. Frontiers in aging neuroscience 7:18.
Kjaergaard M & Kragelund BB (2017) Functions of intrinsic disorder in transmembrane proteins. Cellular and Molecular Life Sciences 74(17):3205-3224.
Shah NH & Aizenman E (2014) Voltage-gated potassium channels at the crossroads of neuronal function, ischemic tolerance, and neurodegeneration. Translational stroke research 5(1):38-58.
Hughes Jr FM & Cidlowski JA (1999) Potassium is a critical regulator of apoptotic enzymes in vitro and in vivo. Advances in enzyme regulation 39(1):157-171.
Yu SP, et al. (1997) Mediation of neuronal apoptosis by enhancement of outward potassium current. Science (New York, N.Y.) 278(5335):114-117.
Yu SP (2003) Regulation and critical role of potassium homeostasis in apoptosis. Progress in neurobiology 70(4):363-386.
Pal S, Hartnett KA, Nerbonne JM, Levitan ES, & Aizenman E (2003) Mediation of neuronal apoptosis by Kv2. 1-encoded potassium channels. Journal of Neuroscience 23(12):4798-4802.
Wu K, Yang P, Li S, Liu C, & Sun F (2015) VEGF attenuated increase of outward delayedrectifier potassium currents in hippocampal neurons induced by focal ischemia via PI3-K pathway. Neuroscience 298:94-101.
Chi XX & Xu ZC (2000) Differential changes of potassium currents in CA1 pyramidal neurons after transient forebrain ischemia. Journal of neurophysiology 84(6):2834-2843.
Redman PT, et al. (2006) A vital role for voltage-dependent potassium channels in dopamine transporter-mediated 6-hydroxydopamine neurotoxicity. Neuroscience 143(1):1-6.
Jiao S, et al. (2007) cAMP/protein kinase A signalling pathway protects against neuronal apoptosis and is associated with modulation of Kv2. 1 in cerebellar granule cells. Journal of neurochemistry 100(4):979-991.
Aizenman E, et al. (2000) Induction of neuronal apoptosis by thiol oxidation: putative role of intracellular zinc release. Journal of neurochemistry 75(5):1878-1888.
Redman PT, Hartnett KA, Aras MA, Levitan ES, & Aizenman E (2009) Regulation of apoptotic potassium currents by coordinated zinc—dependent signalling. The Journal of physiology 587(18):4393-4404.

(Continued)

*Primary Examiner* — Kristin A Vajda
(74) *Attorney, Agent, or Firm* — Meunier Carlin & Curfman LLC

(57) ABSTRACT

Disclosed herein are small molecule compounds capable of disrupting Kv2.1-syntaxin binding. The compounds are useful for treating a variety of neurological disorders, diseases, and injuries.

17 Claims, 16 Drawing Sheets

(56) References Cited

OTHER PUBLICATIONS

Redman PT, et al. (2007) Apoptotic surge of potassium currents is mediated by p38 phosphorylation of Kv2. 1. Proceedings of the National Academy of Sciences 104(9):3568-3573.
He K, McCord MC, Hartnett KA, & Aizenman E (2015) Regulation of pro-apoptotic phosphorylation of Kv2. 1 K+ channels. PloS one 10(6):e0129498.
McCord MC & Aizenman E (2013) Convergent Ca2+ and Zn2+ signaling regulates apoptotic Kv2. 1 K+ currents. Proceedings of the National Academy of Sciences 110(34):13988-13993.
Pal S, Takimoto K, Aizenman E, & Levitan ES (2006) Apoptotic surface delivery of K+channels. Cell Death & Differentiation 13(4):661-667.
Singer-Lahat D, et al. (2007) K+ channel facilitation of exocytosis by dynamic interaction with syntaxin. Journal of Neuroscience 27(7):1651-1658.
Singer-Lahat D, Chikvashvili D, & Lotan I (2008) Direct interaction of endogenous Kv channels with syntaxin enhances exocytosis by neuroendocrine cells. PLoS One 3(1):e1381.
Leung YM, et al. (2003) Syntaxin 1A binds to the cytoplasmic C terminus of Kv2. 1 to regulate channel gating and trafficking. Journal of Biological Chemistry 278(19):17532-17538.
McCord MC & Aizenman E (2014) The role of intracellular zinc release in aging, oxidative stress, and Alzheimer's disease. Front Aging Neurosci 6:77.
Yeh C-Y, et al. (2017) Targeting a Potassium Channel/Syntaxin Interaction Ameliorates Cell Death in Ischemic Stroke. Journal of Neuroscience 37(23):5648-5658.
Pabon NA & Camacho CJ (2017) Probing protein flexibility reveals a mechanism for selective promiscuity. Elife 6:e22889.
Toonen RF & Verhage M (2007) Munc18-1 in secretion: lonely Munc joins SNARE team and takes control. Trends in neurosciences 30(11):564-572.
Burkhardt P, Hattendorf DA, Weis WI, & Fasshauer D (2008) Munc18a controls SNARE assembly through its interaction with the syntaxin N—peptide. The EMBO journal 27(7):923-933.
Jiao J, et al. (2018) Munc18-1 catalyzes neuronal SNARE assembly by templating SNARE association. eLife 7:e41771.
Koes DR, Baumgartner MP, & Camacho CJ (2013) Lessons learned in empirical scoring with smina from the CSAR 2011 benchmarking exercise. Journal of chemical information and modeling 53(8):1893-1904.
Koes DR & Camacho CJ (2012) ZINCPharmer: pharmacophore search of the ZINC database. Nucleic acids research 40(W1):W409-W414.
Irwin JJ & Shoichet BK (2005) Zinc—A free database of commercially available compounds for virtual screening. Journal of chemical information and modeling 45(1):177-182.
Ye Z, Baumgartner MP, Wingert BM, & Camacho CJ (2016) Optimal strategies for virtual screening of induced-fit and flexible target in the 2015 D3R Grand Challenge. Journal of computer-aided molecular design 30(9):695-706.
Aras M, Hartnett K, & Aizenman E (2008) Assessment of cell viability in primary neuronal cultures. Current protocols in neuroscience/editorial board, Jacqueline N. Crawley . . . [ et al.]:Unit 7.18.
Shimamoto K, et al. (1998) DL-threo-β-benzyloxyaspartate, a potent blocker of excitatory amino acid transporters. Molecular pharmacology 53(2):195-201.
Justice JA, et al. (2018) Molecular Neuroprotection Induced by Zinc-Dependent Expression of Hepatitis C-Derived Protein NS5A Targeting Kv2. 1 Potassium Channels. Journal of Pharmacology and Experimental Therapeutics 367(2):348-355.
Blitzblau R, Gupta S, Djali S, Robinson MB, & Rosenberg PA (1996) The glutamate transport inhibitor 1—trans—pyrrolidine—2, 4—dicarboxylate indirectly evokes NMDA receptor mediated neurotoxicity in rat cortical cultures. European Journal of Neuroscience 8(9):1840-1852.
Sattler R & Tymianski M (2001) Molecular mechanisms of glutamate receptor-mediated excitotoxic neuronal cell death. Molecular neurobiology 24(1-3):107-129.
Choi DW (1987) Ionic dependence of glutamate neurotoxicity. Journal of Neuroscience 7(2):369-379.
Misura KM, Scheller RH, & Weis WI (2000) Three-dimensional structure of the neuronal-Sec1-syntaxin 1a complex. Nature 404(6776):355.
Verhage M, et al. (2000) Synaptic assembly of the brain in the absence of neurotransmitter secretion. Science (New York, N.Y.) 287(5454):864-869.
Weimer RM, et al. (2003) Defects in synaptic vesicle docking in unc-18 mutants. Nature neuroscience 6(10):1023-1030.
Joshi A, et al. (2015) Cell-specific activity-dependent fractionation of layer ⅔→5B excitatory signaling in mouse auditory cortex. Journal of Neuroscience 35(7):3112-3123.
Joshi A, Kalappa BI, Anderson CT, & Tzounopoulos T (2016) Cell-specific cholinergic modulation of excitability of layer 5B principal neurons in mouse auditory cortex. Journal of Neuroscience 36(32):8487-8499.
Shen J, Rathore SS, Khandan L, & Rothman JE (2010) SNARE bundle and syntaxin N-peptide constitute a minimal complement for Munc18-1 activation of membrane fusion. The Journal of cell biology 190(1):55-63.
Jensen CS, et al. (2017) Trafficking of Kv2. 1 Channels to the Axon Initial Segment by a Novel Nonconventional Secretory Pathway. Journal of Neuroscience 37(48):11523-11536.
Ballarin B & Tymianski M (2018) Discovery and development of NA-1 for the treatment of acute ischemic stroke. Acta Pharmacologica Sinica.
McCord MC & Aizenman E (2014) The role of intracellular zinc release in aging, oxidative stress, and Alzheimer's disease. Frontiers in aging neuroscience 6:77.
Wei Y, Shin MR, & Sesti F (2018) Oxidation of KCNB1 channels in the human brain and in mouse model of Alzheimer's disease. Cell death & disease 9(8):820.
Chao RY, Cheng CH, Wu SN, & Chen PC (2018) Defective trafficking of Kv2. 1 channels in MPTP—induced nigrostriatal degeneration. Journal of neurochemistry 144(4):483-497.
Liu Z, Zhou T, Ziegler AC, Dimitrion P, & Zuo L (2017) Oxidative stress in neurodegenerative diseases: from molecular mechanisms to clinical applications. Oxidative medicine and cellular longevity 2017.
Götz, A. W. et al. Routine microsecond molecular dynamics simulations with AMBER on GPUs. 1. Generalized born. Journal of chemical theory and computation 8, 1542-1555 (2012).
Jorgensen, W. L., Chandrasekhar, J., Madura, J. D., Impey, R. W. & Klein, M. L. Comparison of simple potential functions for simulating liquid water. The Journal of chemical physics 79, 926-935 (1983).
Loncharich, R. J., Brooks, B. R. & Pastor, R. W. Langevin dynamics of peptides: The frictional dependence of isomerization rates of N-acetylalanyl-N'-methylamide. Biopolymers: Original Research on Biomolecules 32, 523-535 (1992).
Berendsen, H. J., Postma, J. v., van Gunsteren, W. F., DiNola, A. & Haak, J. Molecular dynamics with coupling to an external bath. The Journal of chemical physics 81, 3684-3690 (1984).
Ryckaert, J.-P., Ciccotti, G. & Berendsen, H. J. Numerical integration of the cartesian equations of motion of a system with constraints: molecular dynamics of n-alkanes. Journal of Computational Physics 23, 327-341 (1977).
McCord, M. C. et al. Syntaxin-binding domain of Kv2. 1 is essential for the expression of apoptotic K+ currents. The Journal of physiology 592, 3511-3521 (2014).
Hartnett, K. et al. NMDA receptor-mediated neurotoxicity: a paradoxical requirement for extracellular Mg2+ in Na+/Ca2+-free solutions in rat cortical neurons in vitro. Journal of neurochemistry 68, 1836-1845 (1997).
Aizenman, E., Hartnett, K. A. & Reynoldst, I. J. Oxygen free radicals regulate NMDA receptor function via a redox modulatory site. Neuron 5, 841-846 (1990).

(56) References Cited

OTHER PUBLICATIONS

Sinor, J. D. et al. NMDA and glutamate evoke excitotoxicity at distinct cellular locations in rat cortical neurons in vitro. Journal of Neuroscience 20, 8831-8837 (2000).
Yeh, C. Y. et al. Targeting a Potassium Channel/Syntaxin Interaction Ameliorates Cell Death in Ischemic Stroke. The Journal of neuroscience : the official journal of the Society for Neuroscience, doi: 10.1523/JNEUROSCI.3811-16.2017 (2017).
Brittain, J. M. et al. Suppression of inflammatory and neuropathic pain by uncoupling CRMP-2 from the presynaptic Ca(2)(+) channel complex. Nature medicine 17, 822-829, doi: 10.1038/nm.2345 (2011).
Wilson, S. M. et al. Further insights into the antinociceptive potential of a peptide disrupting the N-type calcium channel-CRMP-2 signaling complex. Channels 5, 449-456, doi:10.4161/chan.5.5.17363 (2011).
Brittain, J. M. et al. Disruption of NMDAR-CRMP-2 signaling protects against focal cerebral ischemic damage in the rat middle cerebral artery occlusion model. Channels 6, 52-59, doi: 10.4161/chan.18919 (2012).
Wilson, S. M. et al. Inhibition of transmitter release and attenuation of anti-retroviral-associated and tibial nerve injury-related painful peripheral neuropathy by novel synthetic Ca2+ channel peptides. The Journal of biological chemistry 287, 35065-35077, doi: 10.1074/jbc.M112.378695 (2012).
Moutal, A. et al. Dissecting the role of the CRMP2-neurofibromin complex on pain behaviors. Pain 158, 2203-2221, doi: 10.1097/j.pain.0000000000001026 (2017).
Francois-Moutal, L. et al. Inhibition of the Ubc9 E2 SUMO-conjugating enzyme-CRMP2 interaction decreases NaV1.7 currents and reverses experimental neuropathic pain. Pain 159, 2115-2127, doi: 10.1097/j.pain.0000000000001294 (2018).
International Search Report and Written Opinion dated Nov. 27, 2019, from International Application No. PCT/US2019/044393, 10 pages.
PubChem SID 254796920 dated Nov. 5, 2019, 8 pages.
PubChem SID 258780605 dated Sep. 4, 2019, 4 pages.

* cited by examiner cpd1 cpd2 cpd3 cpd4 cpd5 cpd6

NEUROPROTECTIVE DISRUPTION OF KV2.1/SYNTAXIN INTERACTION BY SMALL MOLECULES

CROSS-REFERENCE TO RELATED APPLICATION

This application claims the benefit of U.S. Provisional Applications 62/712,514, filed on Jul. 31, 2018, and 62/716,734, filed Aug. 9, 2018, the contents of each are hereby incorporated in its entirety.

STATEMENT OF GOVERNMENT SUPPORT

This invention was made with government support under NS043277 and GM097082 awarded by the National Institutes of Health. The government has certain rights in the invention.

FIELD OF THE INVENTION

The invention is directed to compounds that modulate intracellular potassium concentrations, and to the use of such compounds for the treatment of neurological injuries and diseases.

BACKGROUND

A critical convergent factor in cell death programs is the modulation of intracellular $K^+$, which, at normal, physiological concentrations, suppresses the activation of several proteases and nucleases linked to cellular injury (Hughes Jr & Cidlowski, 1999). Indeed, enhanced $K^+$ efflux following injurious stimuli can rapidly deplete intracellular $K^+$, thereby enabling the completion of cell death cascades (Yu et al., 1997; Yu, 2003). This $K^+$ outflow is mediated by the delayed rectifier potassium channel Kv2.1 in several neuronal subtypes, including cortical neurons (Pal et al., 2003), hippocampal pyramidal neurons (Chi & Xu, 2000; Wu et al., 2015), midbrain dopaminergic neurons (Redman et al., 2006), and cerebellar granule cells (Jiao et al., 2007). Upstream of Kv2.1-facilitated cell death programs, oxidative and nitrosative stress accompanying most forms of acute or chronic neuronal injury liberate intracellular zinc from metal binding proteins. This rise in zinc initiates an enzymatic cascade leading to the sequential phosphorylation of Kv2.1 residues Y124 and S800 by Src and p38 kinases, respectively (Redman et al., 2007; Redman et al., 2009; He et al., 2015). This dual phosphorylation of the channel enhances its interaction with the SNARE protein syntaxin 1A (syntaxin), leading to increased surface expression of active Kv2.1 and the subsequent intracellular $K^+$ loss (Pal et al, 2003; Pal et al, 2006; Redman et al, 2006; McCord & Aizenman, 2013; Shah & Aizenman, 2014). This series of events appear to be exclusively associated with cell death processes and thereby represent a promising target for novel neuroprotective strategies (McCord et al, 2014; Yeh et al, 2017).

The domain within Kv2.1 responsible for its interaction with syntaxin is located within the Kv2.1 proximal cytosolic c-terminal, termed C1a (Singer-Lahat et al., 2007). Overexpression of a protein fragment containing residues 441-522 within the C1a (Kv2.1 rat sequence; accession #NP_037318.1) is sufficient to inhibit the injury-induced plasma membrane insertion of Kv2.1 channels in neurons and provide neuroprotection in vitro (McCord et al, 2014). More recently, our laboratory narrowed down the amino acid sequence within C1a to 9 residues, HLSPNKWKW (C1aB; from N- to C-terminus, corresponding to Kv2.1 residues 478-486 in rat, and 482-490 in mouse and humans (Accession #s NP_032446.2 and NP_004966.1, respectively). The conjugation of this sequence to a cell-permeant domain yielded a blood brain barrier-permeable peptide (TAT-C1aB) that effectively ameliorated acute neuronal injury in vivo (Yeh et al., 2017).

Although TAT-C1aB represents an intriguing therapeutic candidate, peptide-based therapeutics possess several innate disadvantages, including poor pharmacokinetic properties and metabolic instability. Thus, there remains a need for improved Kv2.1-syntaxin binding disrupters.

SUMMARY

Disclosed herein are small molecule Kv2.1-syntaxin binding disrupters.

The details of one or more embodiments are set forth in the descriptions below. Other features, objects, and advantages will be apparent from the description and from the claims.

DETAILED DESCRIPTION

Figure 1:
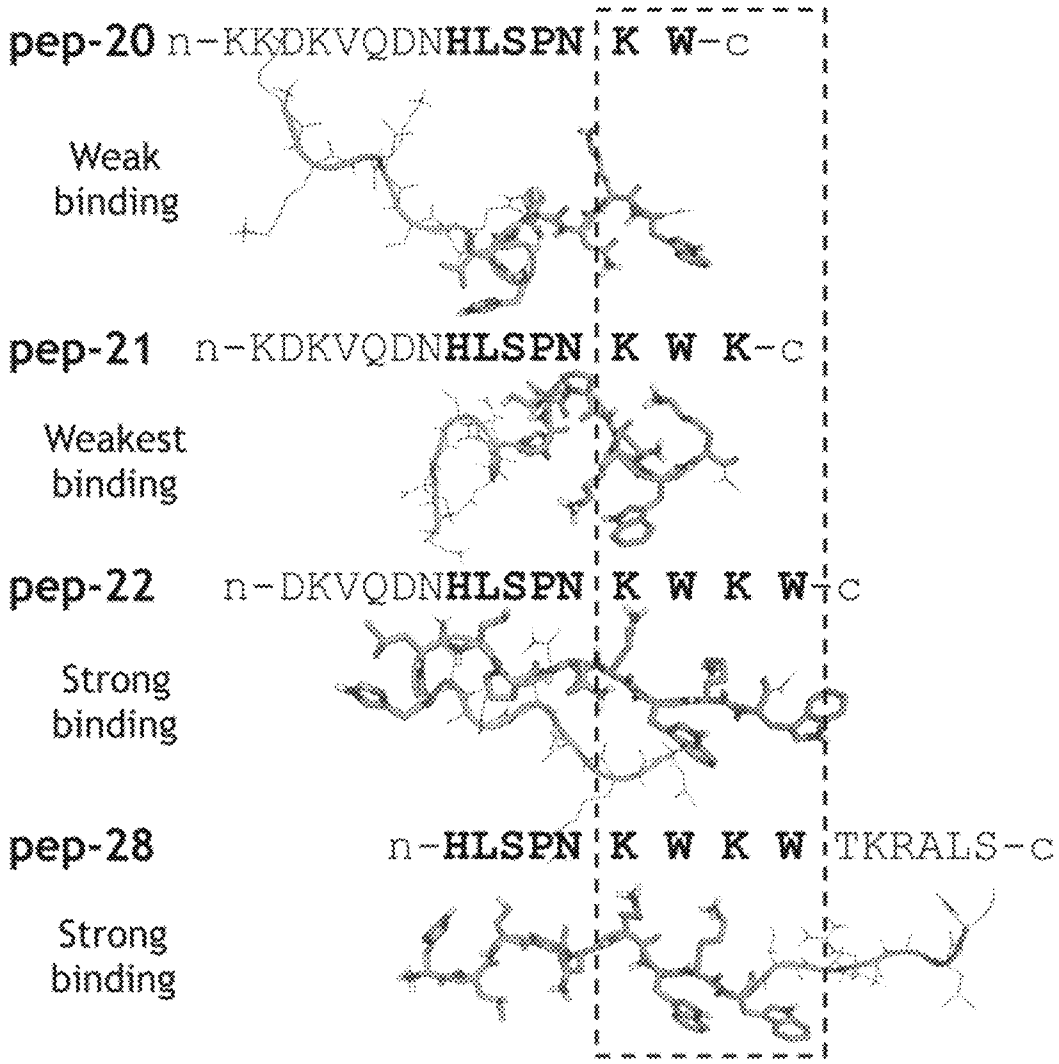
FIG. 1 depicts representative molecular dynamics snapshots of four Kv2.1-derived peptides labelled with their respective binding strength. From first row down, Kv2.1 peptides containing: sequence up to the second KW motif, sequence up to the K of the second KW motif, sequence inclusive of the entire C1aB, natural Kv2.1 residues of the region.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes¬ from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The term "alkyl" as used herein is a branched or unbranched hydrocarbon group such as methyl, ethyl, n-propyl, isopropyl, n-butyl, isobutyl, t-butyl, pentyl, hexyl, heptyl, octyl, nonyl, decyl, dodecyl, and the like. The alkyl group can also be substituted or unsubstituted. Unless stated otherwise, the term "alkyl" contemplates both substituted and unsubstituted alkyl groups. The alkyl group can be substituted with one or more groups including, but not limited to, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol. An alkyl group which contains no double or triple carbon-carbon bonds is designated a saturated alkyl group, whereas an alkyl group having one or more such bonds is designated an unsaturated alkyl group. Unsaturated alkyl groups having a double bond can be designated alkenyl groups, and unsaturated alkyl groups having a triple bond can be designated alkynyl groups. Unless specified to the contrary, the term alkyl embraces both saturated and unsaturated groups.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is replaced with a heteroatom such as, but not limited to, nitrogen, oxygen, sulfur, selenium or phosphorus. The cycloalkyl group and heterocycloalkyl group can be substituted or unsubstituted. Unless stated otherwise, the terms "cycloalkyl" and "heterocycloalkyl" contemplate both substituted and unsubstituted cyloalkyl and heterocycloalkyl groups. The cycloalkyl group and heterocycloalkyl group can be substituted with one or more groups including, but not limited to, alkyl, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol. A cycloalkyl group which contains no double or triple carbon-carbon bonds is designated a saturated cycloalkyl group, whereas an cycloalkyl group having one or more such bonds (yet is still not aromatic) is designated an unsaturated cycloalkyl group. Unless specified to the contrary, the term cycloalkyl embraces both saturated and unsaturated, non-aromatic, ring systems.

The term "aryl" as used herein is an aromatic ring composed of carbon atoms. Examples of aryl groups include, but are not limited to, phenyl and naphthyl, etc. The term "heteroaryl" is an aryl group as defined above where at least one of the carbon atoms of the ring is replaced with a heteroatom such as, but not limited to, nitrogen, oxygen, sulfur, selenium or phosphorus. The aryl group and heteroaryl group can be substituted or unsubstituted. Unless stated otherwise, the terms "aryl" and "heteroaryl" contemplate both substituted and unsubstituted aryl and heteroaryl groups. The aryl group and heteroaryl group can be substituted with one or more groups including, but not limited to, alkyl, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol.

Exemplary heteroaryl and heterocyclyl rings include: benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyL cirrnolinyl, decahydroquinolinyl, 2H,6H~1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl.

The terms "alkoxy," "cycloalkoxy," "heterocycloalkoxy," "cycloalkoxy," "aryloxy," and "heteroaryloxy" have the aforementioned meanings for alkyl, cycloalkyl, heterocycloalkyl, aryl and heteroaryl, further providing said group is connected via an oxygen atom.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. Unless specifically stated, a substituent that is said to be "substituted" is meant that the substituent can be substituted with one or more of the following: alkyl, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol. In a specific example, groups that are said to be substituted are substituted with a protic group, which is a group that can be protonated or deprotonated, depending on the pH.

Unless specified otherwise, the term "patient" refers to any mammalian animal, including but not limited to, humans.

Pharmaceutically acceptable salts are salts that retain the desired biological activity of the parent compound and do not impart undesirable toxicological effects. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, p-toluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate. Pharmaceutically acceptable and non-pharmaceutically acceptable salts may be prepared using procedures well known in the art, for example, by reacting a sufficiently basic compound such as an amine with a suitable acid comprising a physiologically acceptable anion. Alkali metal (for example, sodium, potassium, or lithium) or alkaline earth metal (for example, calcium) salts of carboxylic acids can also be made.

Disclosed herein are compounds having the formula:

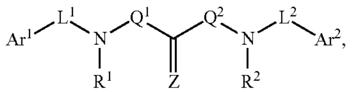

and pharmaceutically acceptable salts thereof, wherein $Ar^1$ and $Ar^2$ are independently aryl and heteroaryl groups;

$L^1$ and $L^2$ are optionally present linking groups;

$R^1$ is selected from $R^{1a}$ or $OR^{1a}$, wherein $R^{1a}$ is selected from hydrogen or $C_{1-8}$alkyl;

$R^2$ is selected from $R^{2a}$ or $OR^{2a}$, wherein $R^{2a}$ is selected from hydrogen or $C_{1-8}$alkyl;

$Q^1$ is absent, or a group having the formula $—CR^{q1}R^{q1'}—$; wherein $R^{q1}$ is selected from $R^{q1a}$, $OR^{q1a}$, $N(R^{q1a})_2$, $SO_2R^{q1a}$, $SO_2N(R^{q1a})_2$, $C(O)R^{q1a}$; $C(O)OR^{q1a}$, $OC(O)R^{q1a}$; $C(O)N(R^{q1a})_2$, $N(R^{q1a})C(O)R^{q1a}$, $OC(O)N(R^{q1a})_2$, $N(R^{q1a})C(O)N(R^{q1a})_2$, wherein $R^{q1a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

$R^{q1}$ is selected from $R^{q1a}$, $OR^{q1a}$, $N(R^{q1a})_2$, $SO_2R^{q1a}$, $SO_2N(R^{q1a})_2$, $C(O)R^{q1a}$; $C(O)OR^{q1a}$, $OC(O)R^{q1'a}$; $C(O)N(R^{q1a})_2$, $N(R^{q1'a})C(O)R^{q1'a}$, $OC(O)N(R^{q1'a})_2$, $N(R^{q1'a})C(O)N(R^{q1'a})_2$, wherein $R^{q1a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

$Q^2$ is absent, or a group having the formula $—CR^{q2}R^{q2'}—$; wherein $R^{q2}$ is selected from $R^{q2a}$, $OR^{q2a}$, $N(R^{q2a})_2$, $SO_2R^{q2a}$, $SO_2N(R^{q2a})_2$, $C(O)R^{q2a}$; $C(O)OR^{q2a}$, $OC(O)R^{q2a}$; $C(O)N(R^{q2a})_2$, $N(R^{q2a})C(O)R^{q2a}$, $OC(O)N(R^{q2a})_2$, $N(R^{q2a})C(O)N(R^{q2a})_2$, wherein $R^{q2a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

$R^{q2'}$ is selected from $R^{q2'a}$, $OR^{q2'a}$, $N(R^{q2'a})_2$, $SO_2R^{q2'a}$, $SO_2N(R^{q2'a})_2$, $C(O)R^{q2'a}$; $C(O)OR^{q2'a}$, $OC(O)R^{q2'a}$; $C(O)N(R^{q2'a})_2$, $N(R^{q2'a})C(O)R^{q2'a}$, $OC(O)N(R^{q2'a})_2$, $N(R^{q2'a})C(O)N(R^{q2'a})_2$, wherein $R^{q2'a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

Z is O, S, or $NR^3$;

$R^3$ is selected from $R^{3a}$, $OR^{3a}$, $N(R^{3a})_2$, $SO_2R^{3a}$, $SO_2N(R^{3a})_2$, $C(O)R^{3a}$; $C(O)OR^{3a}$, $OC(O)R^{3a}$; $C(O)N(R^{3a})_2$, $N(R^{3a})C(O)R^{3a}$, $OC(O)N(R^{3a})_2$, $N(R^{3a})C(O)N(R^{3a})_2$, wherein $R^{3a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

wherein any two or more of $R^1$, $R^2$, $R^3$, $L^1$, $L^2$, $Ar^1$, or $Ar^2$ may together form a ring.

Suitable aryl and heteroaryl groups include those having the formula:

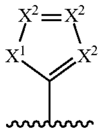 or 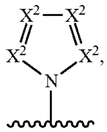, wherein $X^1$ is O, Se, Se, $NR^x$, or an olefin having the formula —C(R)=C(R)—; $X^2$ is CR or N;

$R^x$ is hydrogen, $C_{1-8}$alkyl, $C_{2-8}$alkenyl, $C_{2-8}$alkynyl, aryl, heteroaryl, $C_{3-8}$cycloalkyl, or $C_{1-8}$heteroaryl;

R is in each case independently selected from $R^a$, $OR^a$, $N(R^a)_2$, $SR^a$, $SO_2R^a$, $SO_2N(R^a)_2$, $C(O)R^a$; $C(O)OR^a$, $OC(O)R^a$; $C(O)N(R^a)_2$, $N(R^a)C(O)R^a$, $OC(O)N(R^a)_2$, $N(R^a)C(O)N(R^a)_2$, wherein $R^a$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl; wherein any two or more of R, $R^a$, $R^x$, $L^1$ or $R^1$ may together form a ring.

Exemplary aryl and heteroaryl groups include monocyclic systems like phenyl, pyridinyl, pyrrolyl, pyrimidinyl, pyrazinyl, furanyl, imidazolyl, triazinyl, oxazolyl, thiazolyl, azepinyl, and diazepinyl; bicyclic systems including benzo-fused variants of the above, including napthyl, quinolinyl, isoquinolinyl, benzofuran, indole, benzothiphene, and the like.

Other groups include purine and pteridine systems; polycyclic systems, e.g., ring systems having three or more fused rings can also be present in the compounds of the invention. Aryl and heteroaryl groups can also be substituted one or more times with groups as defined herein.

In some embodiments, $Ar^1$ can be a monocyclic group having the structure:

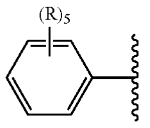, 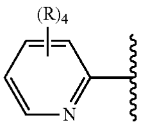, 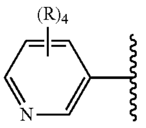,

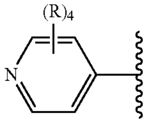, 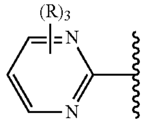, 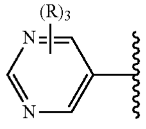,

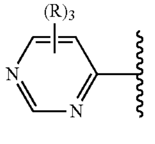 or 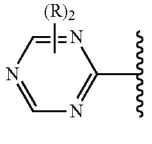, wherein R is in each case independently selected from $R^a$, $OR^a$, $N(R^a)_2$, $SR^a$, $SO_2R^a$, $SO_2N(R^a)_2$, $C(O)R^a$; $C(O)OR^a$, $OC(O)R^a$; $C(O)N(R^a)_2$, $N(R^a)C(O)R^a$, $OC(O)N(R^a)_2$, $N(R^a)C(O)N(R^a)_2$, wherein $R^a$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

wherein any two or more of R, $R^a$, $R^x$, $L^1$ or $R^1$ may together form a ring.

In certain embodiments, $Ar^1$ has the structure:

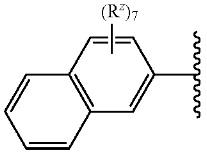, 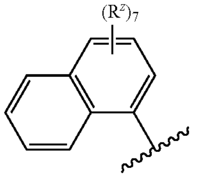,

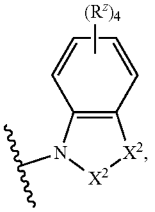 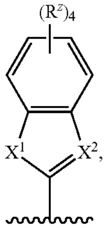 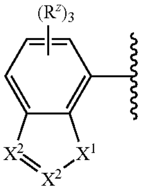, or

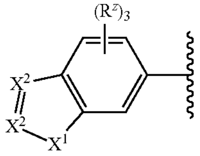, wherein $X^1$ is O, Se, Se, $NR^x$, or an olefin having the formula —C(R)=C(R)—, $X^2$ is CR, or N;

$R^x$ is hydrogen, $C_{1-8}$alkyl, $C_{2-8}$alkenyl, $C_{2-8}$alkynyl, aryl, heteroaryl, $C_{3-8}$cycloalkyl, and $C_{1-8}$heteroaryl;

$R^z$ is in each case independently selected from $R^{za}$, $OR^{za}$, $N(R^{za})_2$, $SR^{za}$, $SO_2R^{za}$, $SO_2N(R^{za})_2$, $C(O)R^{za}$; $C(O)OR^{za}$, $OC(O)R^{za}$; $C(O)N(R^{za})_2$, $N(R^{za})C(O)R^{za}$, $OC(O)N(R^{za})_2$, $N(R^{za})C(O)N(R^{za})_2$, wherein $R^{za}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

wherein any two or more of R, $R^{za}$, $R^x$, $L^1$ or $R^1$ may together form a ring.

In certain preferred embodiments, $Ar^1$ is a phenyl group having the structure:

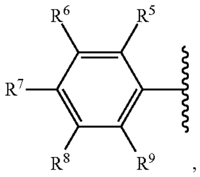, wherein, $R^5$ is selected from $R^{5a}$, $OR^{5a}$, $N(R^{5a})_2$, $SiR^{5a}_3$, $SR^{5a}$, $SO_2R^{5a}$, $SO_2N(R^{5a})_2$, $C(O)R^{5a}$; $C(O)OR^{5a}$, $OC(O)R^{5a}$; $C(O)N(R^{5a})_2$, $N(R^{5a})C(O)R^{5a}$, $OC(O)N(R^{5a})_2$, $N(R^{5a})C(O)N(R^{5a})_2$, F, Cl, Br, I, cyano, and nitro, wherein $R^{5a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

$R^6$ is selected from $R^{6a}$, $OR^{6a}$, $N(R^{6a})_2$, $SiR^{6a}_3$, $SR^{6a}$, $SO_2R^{6a}$, $SO_2N(R^{6a})_2$, $C(O)R^{6a}$; $C(O)OR^{6a}$, $OC(O)R^{6a}$; $C(O)N(R^{6a})_2$, $N(R^{6a})C(O)R^{6a}$, $OC(O)N(R^{6a})_2$, $N(R^{6a})C(O)N(R^{6a})_2$, F, Cl, Br, I, cyano, and nitro, wherein $R^{6a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

$R^7$ is selected from $R^{7a}$, $OR^{7a}$, $N(R^{7a})_2$, $SiR^{7a}{}_3$, $SR^{7a}$, $SO_2R^{7a}$, $SO_2N(R^{7a})_2$, $C(O)R^{7a}$; $C(O)OR^{7a}$, $OC(O)R^{7a}$; $C(O)N(R^{7a})_2$, $N(R^{7a})C(O)R^{7a}$, $OC(O)N(R^{7a})_2$, $N(R^{7a})C(O)N(R^{7a})_2$, F, Cl, Br, I, cyano, and nitro, wherein $R^{7a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

$R^8$ is selected from $R^{8a}$, $OR^{8a}$, $N(R^{8a})_2$, $SiR^{8a}{}_3$, $SR^{8a}$, $SO_2R^{8a}$, $SO_2N(R^{8a})_2$, $C(O)R^{8a}$; $C(O)OR^{8a}$, $OC(O)R^{8a}$; $C(O)N(R^{8a})_2$, $N(R^{8a})C(O)R^{8a}$, $OC(O)N(R^{8a})_2$, $N(R^{8a})C(O)N(R^{8a})_2$, F, Cl, Br, I, cyano, and nitro, wherein $R^{8a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

$R^9$ is selected from $R^{9a}$, $OR^{9a}$, $N(R^{9a})_2$, $SiR^{9a}{}_3$, $SR^{9a}$, $SO_2R^{9a}$, $SO_2N(R^{9a})_2$, $C(O)R^{9a}$; $C(O)OR^{9a}$, $OC(O)R^{9a}$; $C(O)N(R^{9a})_2$, $N(R^{9a})C(O)R^{9a}$, $OC(O)N(R^{9a})_2$, $N(R^{9a})C(O)N(R^{9a})_2$, F, Cl, Br, I, cyano, and nitro, wherein $R^{9a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

wherein any two or more of $L^1$, $R^1$, $R^5$, $R^6$, $R^7$, $R^8$, and $R^9$ may together form a ring.

Various substitution patterns can be present in $Ar^1$. $Ar^1$ can be a monosubstituted aryl or heteroaryl ring. For instance, in some embodiments each of $R^6$, $R^7$, $R^8$, and $R^9$ are hydrogen, and $R^5$ is as defined above; each of $R^5$, $R^7$, $R^8$, and $R^9$ are hydrogen, and $R^6$ is as defined above; each of $R^5$, $R^6$, $R^8$, and $R^9$ are hydrogen, and $R^7$ is as defined above; each of $R^5$, $R^6$, $R^7$, and $R^9$ are hydrogen, and $R^8$ is as defined above; or each of $R^5$, $R^6$, $R^7$, and $R^8$ are hydrogen, and $R^9$ is as defined above. In other embodiments, $Ar^1$ can be a disubstituted aryl or heteroaryl ring. For instance, in some embodiments each of $R^7$, $R^8$, and $R^9$ are hydrogen, and $R^5$ and $R^6$ are as defined above; each of $R^6$, $R^8$, and $R^9$ are hydrogen, and $R^5$ and $R^7$ are as defined above; each of $R^6$, $R^7$, and $R^9$ are hydrogen, and $R^5$ and $R^8$ are as defined above; each of $R^6$, $R^7$, and $R^8$ are hydrogen, and $R^5$ and $R^9$ are as defined above; each of $R^5$, $R^8$, and $R^9$ are hydrogen, and $R^6$ and $R^7$ are as defined above; each of $R^5$, $R^7$, and $R^9$ are hydrogen, and $R^6$ and $R^8$ are as defined above; or each of $R^5$, $R^7$, and $R^8$ are hydrogen, and $R^6$ and $R^9$ are as defined above.

Particularly preferred $R^5$, $R^6$, $R^7$, $R^8$, and $R^9$ groups include $C_{1-4}$alkyl (e.g., methyl, ethyl, n-propyl, isopropyl, n-butyl, sec-butyl, and isobutyl), $C_{1-4}$alkoxy (e.g., methoxy, ethoxy, n-propoxy, isopropoxy, n-butoxy, sec-butoxy, and isobutoxy), $C_{1-4}$haloalkyl (including, but not limited to trifluromethyl, 2,2,2-trifluoroethyl, and the like), $C_{1-4}$haloalkoxy (including, but not limited to trifluromethoxy, 2,2,2-trifluoroethoxy, and the like), F, Cl, Br, or I.

In certain embodiments, two of $R^5$, $R^6$, $R^7$, $R^8$, and $R^9$ are alkoxy, and together form a ring. For instance, $R^6$ and $R^7$ can each be alkoxy and can together form a ring:

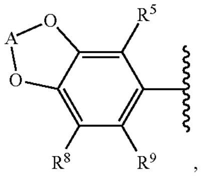
, wherein A is an optionally substituted $C_{1-4}$alkyl group, for instance $CH_2$ or $CH_2CH_2$. In other embodiments, $R^5$ and $R^6$ are each alkoxy and can together form a ring.

In certain embodiments, $Ar^1$ can be group having the formula:

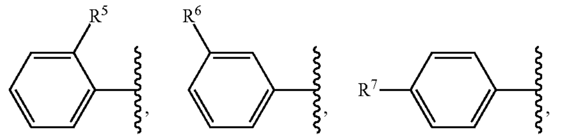

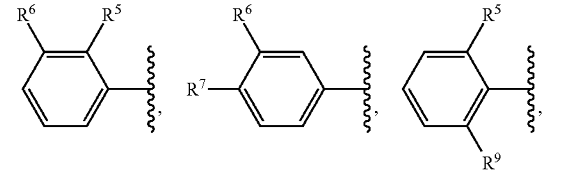

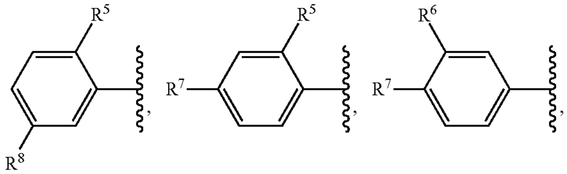

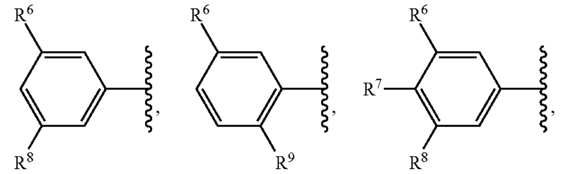

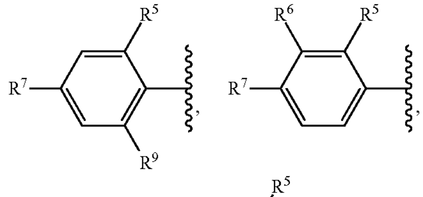
or

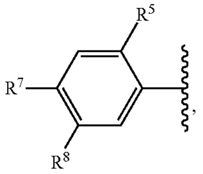

wherein $R^5$, $R^6$, $R^7$, $R^8$, and $R^9$ have the aforementioned meanings. In certain embodiments $R^5$, $R^6$, $R^7$, $R^8$, and $R^9$ can be independently selected from $C_{1-4}$alkyl, $C_{1-4}$alkoxy, $C_{1-4}$haloalkyl, $C_{1-4}$haloalkoxy, F, Cl, Br, or I.

In other embodiments, one or more of $R^5$, $R^6$, $R^7$, $R^8$, and $R^9$ is a poly(ethylene glycol) moiety having the formula $R—(OCH_2CH_2)_n—O—$, wherein R is hydrogen or $C_{1-4}$alkyl, and n is 1, 2, 3, 4, 5, 6, 7, 8, 9, 10, 11, 12, 13, 14, 15, 16, 17, 18, 19, or 20. In other embodiments, n is a number greater than 20. In some instances, $R^5$, $R^8$ and $R^9$ are each hydrogen, and $R^6$ and $R^7$ are a poly(ethylene glycol) moiety as defined above.

$L^1$, when present, can be an optionally substituted $C_{1-8}$alkyl group; an optionally substituted $C_{2-8}$alkenyl group; an optionally substituted $C_{2-8}$alkynyl group; an optionally substituted aryl group; an optionally substituted $C_{1-8}$heteroaryl group; an optionally substituted $C_{3-8}$cycloalky group; or an optionally substituted $C_{1-8}$heterocyclyl group. Substituents on the $L^1$ group can form a ring with any of $R^1$, $R^2$, $R^3$, $L^2$, $Ar^1$, or $Ar^2$.

In some instance, $L^1$ includes a ring system, which can be aryl, heteroaryl, cycloalkyl, and heterocyclyl. For instance, $L^1$ can be an aromatic system having the formula:

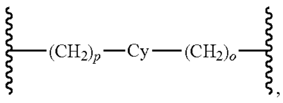, wherein p can be 0, 1, 2, 3, 4, 5, or 6;

can be 0, 1, 2, 3, 4, 5, or 6; and

Cy is an optionally substituted aryl group; an optionally substituted $C_{1-8}$heteroaryl group; an optionally substituted $C_{3-8}$cycloalkyl group; or an optionally substituted $C_{1-8}$heterocyclyl group. Exemplary Cy systems include cyclopropane, cyclobutane, cyclopentane, cyclohexane, cycloheptane, cyclooctane, and various bicyclo and tricyclo derivatives thereof, oxirane, oxetane, dihydrofuran, tetrahydrofuran, pyrrolidine, imidazolidine, oxazolidine, thiazolidine, dioxolane, dithiolane, tetrazole, oxazole, imidazole, thiazole, piperidine, tetrahydropyran, piperazine, pyridine, morpholine, dioxane, azepane, oxepane, azepine, oxepine, and others. The $—(CH_2)_P—$ and $—(CH_2)_o—$ groups may be bonded to a ring carbon or nitrogen.

In some embodiments, $L^1$ is a group having the formula $—(CR^4R^{4'})_n—$, wherein:

n is 0, 1, 2, 3, 4, 5, 6, 7, or 8;

$R^4$ is in each case independently selected from $R^{4a}$, $OR^{4a}$, $N(R^{4a})_2$, $SiR^{4a}_3$, $SR^{4a}$, $SO_2R^{4a}$, $SO_2N(R^{4a})_2$, $C(O)R^{4a}$; $C(O)OR^{4a}$, $OC(O)R^{4a}$; $C(O)N(R^{4a})_2$, $N(R^{4a})C(O)R^{4a}$, $OC(O)N(R^{4a})_2$, $N(R^{4a})C(O)N(R^{4a})_2$, F, Cl, Br, I, cyano, and nitro, wherein $R^{4a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

$R^{4'}$ is in each case independently selected from $R^{4'a}$, $OR^{4'a}$, $N(R^{4'a})_2$, $SiR^{4'a}_3$, $SR^{4'a}$, $SO_2R^{4'a}$, $SO_2N(R^{4'a})_2$, $C(O)R^{4'a}$; $C(O)OR^{4'a}$, $OC(O)R^{4'a}$; $C(O)N(R^{4'a})_2$, $N(R^{4'a})C(O)R^{4'a}$, $OC(O)N(R^{4'a})_2$, $N(R^{4'a})C(O)N(R^{4'a})_2$, F, Cl, Br, I, cyano, and nitro, wherein $R^{4'a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

wherein any two of $R^4$ and $R^{4'}$ may together form a carbonyl, imine, double bond, or triple bond; and wherein any two or more of $R^1$, $R^3$, $R^4$, $R^{4'}$, $R^5$, $R^6$, $R^7$, $R^8$, and $R^9$ may together form a ring. In certain embodiments, $R^4$ and $R^{4'}$ are in each case hydrogen. In further embodiments, $R^4$ and $R^{4'}$ are in each case hydrogen, and n is 1, 2, or 3. In other embodiments, $L^1$ is absent, e.g., n is 0.

$L^2$, when present, can be an optionally substituted $C_{1-8}$alkyl group; an optionally substituted $C_{2-8}$alkenyl group; an optionally substituted $C_{2-8}$alkynyl group; an optionally substituted aryl group; an optionally substituted $C_{1-8}$heteroaryl group; an optionally substituted $C_{3-8}$cycloalky group; or an optionally substituted $C_{1-8}$heterocyclyl group. Substituents on the $L^2$ group can form a ring with any of $R^1$, $R^2$, $R^3$, $L^1$, $Ar^1$, or $Ar^2$.

In some instance, $L^2$ includes a ring system, which can be aryl, heteroaryl, cycloalkyl, and heterocyclyl. For instance, $L^2$ can be an aromatic system having the formula:

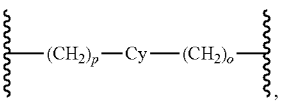, wherein p can be 0, 1, 2, 3, 4, 5, or 6;

can be 0, 1, 2, 3, 4, 5, or 6; and

Cy is an optionally substituted aryl group; an optionally substituted $C_{1-8}$heteroaryl group; an optionally substituted $C_{3-8}$cycloalkyl group; or an optionally substituted $C_{1-8}$heterocyclyl group. Exemplary Cy systems include cyclopropane, cyclobutane, cyclopentane, cyclohexane, cycloheptane, cyclooctane, and various bicyclo and tricyclo derivatives thereof, oxirane, oxetane, dihydrofuran, tetrahydrofuran, pyrrolidine, imidazolidine, oxazolidine, thiazolidine, dioxolane, dithiolane, tetrazole, oxazole, imidazole, thiazole, piperidine, tetrahydropyran, piperazine, pyridine, morpholine, dioxane, azepane, oxepane, azepine, oxepine, and others. The $—(CH_2)_P—$ and $—(CH_2)_o—$ groups may be bonded to a ring carbon or nitrogen.

In some embodiments, $L^2$ is a group having the formula $—(CR^{10}R^{10'})_{n'}—$, wherein:

n' is from 0-8;

$R^{10}$ is in each case independently selected from $R^{10a}$, $OR^{10a}$, $N(R^{10a})_2$, $SiR^{10a}_3$, $SR^{10a}$, $SO_2R^{10a}$, $SO_2N(R^{10a})_2$, $C(O)R^{10a}$; $C(O)OR^{10a}$, $OC(O)R^{10a}$; $C(O)N(R^{10a})_2$, $N(R^{10a})C(O)R^{10a}$, $OC(O)N(R^{10a})_2$, $N(R^{10a})C(O)N(R^{10a})_2$, F, Cl, Br, I, cyano, and nitro, wherein $R^{10a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

$R^{10'}$ is in each case independently selected from $R^{10'a}$, $OR^{10'a}$, $N(R^{10'a})_2$, $SiR^{10'a}_3$, $SR^{10'a}$, $SO_2R^{10'a}$, $SO_2N(R^{10'a})_2$, $C(O)R^{10'a}$; $C(O)OR^{10'a}$, $OC(O)R^{10'a}$; $C(O)N(R^{10'a})_2$, $N(R^{10'a})C(O)R^{10'a}$, $OC(O)N(R^{10'a})_2$, $N(R^{10'a})C(O)N(R^{10'a})_2$, F, Cl, Br, I, cyano, and nitro, wherein $R^{10'a}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl;

wherein any two of $R^{10}$ and $R^{10'}$ may together form a carbonyl, imine, double bond or triple bond; and wherein any two or more of $R^1$, $R^3$, $Ar^2$, $R^{10}$, and $R^{10}$ may together form a ring.

In certain embodiments, $L^2$ is absent, e.g., n' is 0.

Exemplary $Ar^2$ groups include aryl and heteroaryl moeities, optionally substituted with one or more further aryl or heteroaryl groups. In some instances, $Ar^2$ has the formula:

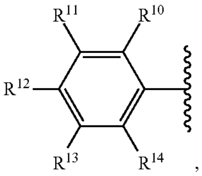, wherein $R^{10}$ is selected from $R^{10a}$, $OR^{10a}$, $N(R^{10a})_2$, $SiR^{10a}_3$, $SR^{10a}$, $SO_2R^{10a}$, $SO_2N(R^{10a})_2$, $C(O)R^{10a}$; $C(O)OR^{10a}$, $OC(O)R^{10a}$; $C(O)N(R^{10a})_2$, $N(R^{10a})C(O)R^{10a}$, $OC(O)N(R^{10a})_2$, $N(R^{10a})C(O)N(R^{10a})_2$, F, Cl, Br, I, cyano, and nitro, wherein $R^{10a}$ is in each case independently selected from hydrogen, $C_{1-13}$alkyl, $C_{2-13}$alkenyl, $C_{2-13}$alkynyl, aryl, $C_{1-8}$heteroaryl, $C_{3-8}$cycloalkyl, or $C_{1-8}$heterocyclyl;

$R^{11}$ is selected from $R^{11a}$, $OR^{11a}$, $N(R^{11a})_2$, $SiR^{11a}_3$, $SR^{11a}$, $SO_2R^{11a}$, $SO_2N(R^{11a})_2$, $C(O)R^{11a}$; $C(O)OR^{11a}$, $OC(O)R^{11a}$; $C(O)N(R^{11a})_2$, $N(R^{11a})C(O)R^{11a}$, $OC(O)N(R^{11a})_2$, $N(R^{11a})C(O)N(R^{11a})_2$, F, Cl, Br, I, cyano, and nitro, wherein $R^{11a}$ is in each case independently selected from hydrogen, $C_{1-13}$alkyl, $C_{2-13}$alkenyl, $C_{2-13}$alkynyl, aryl, $C_{1-8}$heteroaryl, $C_{3-8}$cycloalkyl, or $C_{1-8}$heterocyclyl;

$R^{12}$ is selected from $R^{12a}$, $OR^{12a}$, $N(R^{12a})_2$, $SiR^{12a}_3$, $SR^{12a}$, $SO_2R^{12a}$, $SO_2N(R^{12a})_2$, $C(O)R^{12a}$; $C(O)OR^{12a}$, $OC(O)R^{12a}$; $C(O)N(R^{12a})_2$, $N(R^{12a})C(O)R^{12a}$, $OC(O)N(R^{12a})_2$, $N(R^{12a})C(O)N(R^{12a})_2$, F, Cl, Br, I, cyano, and nitro, wherein $R^{12a}$ is in each case independently selected from hydrogen, $C_{1-13}$alkyl, $C_{2-13}$alkenyl, $C_{2-13}$alkynyl, aryl, $C_{1-8}$heteroaryl, $C_{3-8}$cycloalkyl, or $C_{1-8}$heterocyclyl;

$R^{13}$ is selected from $R^{13a}$, $OR^{13a}$, $N(R^{13a})_2$, $SiR^{13a}_3$, $SR^{13a}$, $SO_2R^{13a}$, $SO_2N(R^{13a})_2$, $C(O)R^{13a}$; $C(O)OR^{13a}$, $OC(O)R^{13a}$; $C(O)N(R^{13a})_2$, $N(R^{13a})C(O)R^{13a}$, $OC(O)N(R^{13a})_2$, $N(R^{13a})C(O)N(R^{13a})_2$, F, Cl, Br, I, cyano, and nitro, wherein $R^{13a}$ is in each case independently selected from hydrogen, $C_{1-13}$alkyl, $C_{2-13}$alkenyl, $C_{2-13}$alkynyl, aryl, $C_{1-8}$heteroaryl, $C_{3-8}$cycloalkyl, or $C_{1-8}$heterocyclyl;

$R^{14}$ is selected from $R^{14a}$, $OR^{14a}$, $N(R^{14a})_2$, $SiR^{14a}_3$, $SR^{14a}$, $SO_2R^{14a}$, $SO_2N(R^{14a})_2$, $C(O)R^{14a}$; $C(O)OR^{14a}$, $OC(O)R^{14a}$; $C(O)N(R^{14a})_2$, $N(R^{14a})C(O)R^{14a}$, $OC(O)N(R^{14a})_2$, $N(R^{14a})C(O)N(R^{14a})_2$, F, Cl, Br, I, cyano, and nitro, wherein $R^{14a}$ is in each case independently selected from hydrogen, $C_{1-13}$alkyl, $C_{2-13}$alkenyl, $C_{2-13}$alkynyl, aryl, $C_{1-8}$heteroaryl, $C_{3-8}$cycloalkyl, or $C_{1-8}$heterocyclyl;

wherein any two or more of $L^1$, $R^1$, $R^3$, $R^{10}$, $R^{11}$, $R^{12}$, $R^{13}$, and $R^{14}$ may together form a ring.

Various substitution patterns can be present in $Ar^2$. $Ar^2$ can be a monosubstituted aryl or heteroaryl ring. For instance, in some embodiments each of $R^{11}$, $R^{12}$, $R^{13}$, and $R^{14}$ are hydrogen, and $R^{10}$ is as defined above; each of $R^{10}$, $R^{12}$, $R^{13}$, and $R^{14}$ are hydrogen, and $R^{11}$ is as defined above; each of $R^{10}$, $R^{11}$, $R^{13}$, and $R^{14}$ are hydrogen, and $R^{12}$ is as defined above; each of $R^{10}$, $R^{11}$, $R^{12}$, and $R^{14}$ are hydrogen, and $R^{13}$ is as defined above; or each of $R^{10}$, $R^{11}$, $R^{12}$, and $R^{13}$ are hydrogen, and $R^{14}$ is as defined above. In other embodiments, $Ar^1$ can be a disubstituted aryl or heteroaryl ring. For instance, in some embodiments each of $R^{12}$, $R^{13}$, and $R^{14}$ are hydrogen, and $R^{10}$ and $R^{11}$ are as defined above; each of $R^{11}$, $R^{13}$, and $R^{14}$ are hydrogen, and $R^{10}$ and $R^{12}$ are as defined above; each of $R^{11}$, $R^{12}$, and $R^{14}$ are hydrogen, and $R^{10}$ and $R^{13}$ are as defined above; each of $R^{11}$, $R^{12}$, and $R^{13}$ are hydrogen, and $R^{10}$ and $R^{14}$ are as defined above; each of $R^{10}$, $R^{13}$, and $R^{14}$ are hydrogen, and $R^{11}$ and $R^{12}$ are as defined above; each of $R^{10}$, $R^{12}$, and $R^{14}$ are hydrogen, and $R^{11}$ and $R^{13}$ are as defined above; or each of $R^{10}$, $R^{12}$, and $R^{13}$ are hydrogen, and $R^{11}$ and $R^{14}$ are as defined above.

Particular preferred $R^{10}$, $R^{11}$, $R^{12}$, $R^{13}$, and $R^{14}$ groups include bicyclic aryl and heteroaryl groups having the formula:

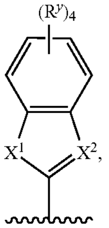,
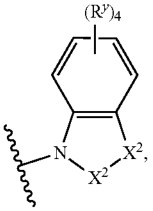,
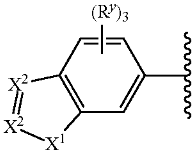, or
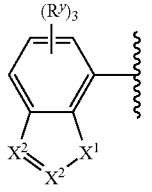, wherein $X^1$ is O, Se, Se, $NR^x$, or an olefin having the formula —C(R)═C(R)—, $X^2$ is CR, or N; $R^x$ is hydrogen, $C_{1-8}$alkyl, $C_{2-8}$alkenyl, $C_{2-8}$alkynyl, aryl, heteroaryl, $C_{3-8}$cycloalkyl, and $C_{1-8}$heteroaryl;

$R^y$ is in each case independently selected from $R^{ya}$, $OR^{ya}$, $N(R^{ya})_2$, $SR^{ya}$, $SO_2R^{ya}$, $SO_2N(R^{ya})_2$, $C(O)R^{ya}$; $C(O)OR^{ya}$, $OC(O)R^{ya}$; $C(O)N(R^{ya})_2$, $N(R^{ya})C(O)R^{ya}$, $OC(O)N(R^{ya})_2$, $N(R^{ya})C(O)N(R^{ya})_2$, wherein $R^{ya}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl; wherein any two or more of R, $R^{ya}$, $R^x$, $R^3$, $L^2$ or $R^2$ may together form a ring.

In certain embodiments, $Ar^2$ can be a group having the formula:

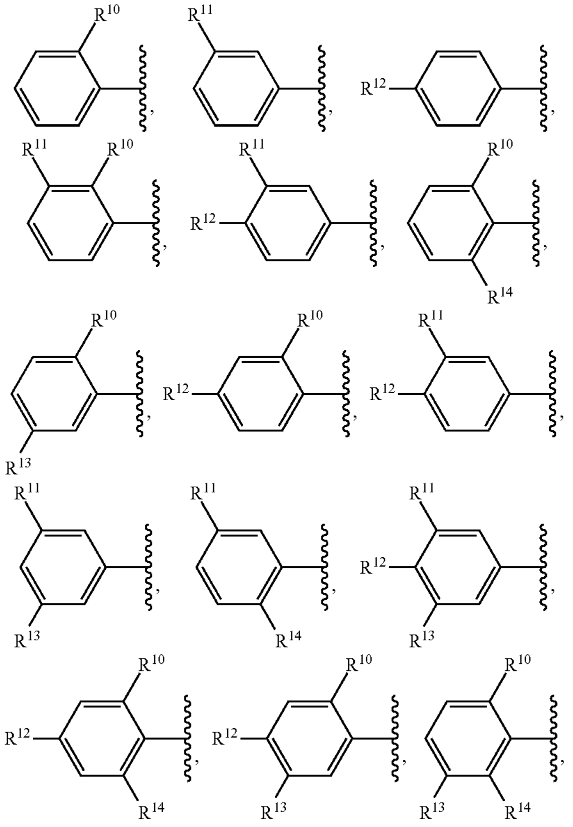

-continued

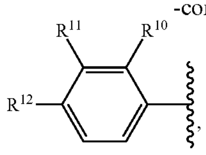, 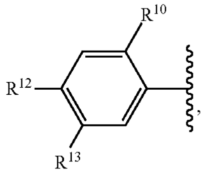,

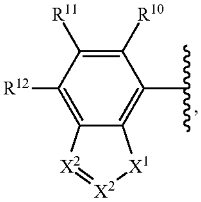, 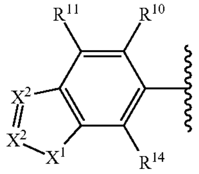

wherein $R^{10}$, $R^{11}$, $R^{12}$, $R^{13}$, and $R^{14}$ have the aforementioned meanings. In certain preferred embodiments, $R^{11}$ or $R^{13}$ can be aryl or $C_{1-8}$heteroaryl. Exemplary $R^{11}$ and $R^{13}$ groups include:

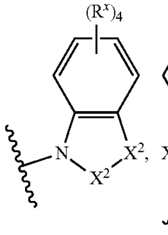, 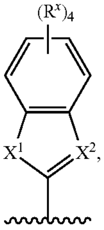, 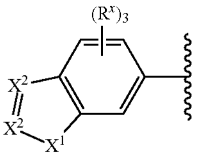, and

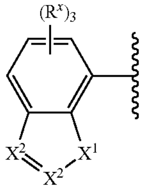

wherein

- $X^1$ is selected from an olefin having the formula —$C(R^x)$=$C(R^x)$—, or a heteroatom such as O, S, Se or $NR^4$;
- $X^2$ is independently selected from $CR^x$ or N;
- $R^4$ is hydrogen, $C_{1-8}$alkyl, $C_{2-8}$alkenyl, $C_{2-8}$alkynyl, aryl, heteroaryl, $C_{3-8}$cycloalkyl, and $C_{1-8}$heteroaryl;
- $R^x$ is in each case independently selected from $R^{xa}$, $OR^{xa}$, $N(R^{xa})_2$, $SO_2R^{xa}$, $SO_2N(R^{xa})_2$, $C(O)R^{xa}$; $C(O)OR^{xa}$, $OC(O)R^{xa}$; $C(O)N(R^{xa})_2$, $N(R^{xa})C(O)R^{xa}$, $OC(O)N(R^{xa})_2$, $N(R^{xa})C(O)N(R^{xa})_2$, wherein $R^{xa}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl; and wherein any two or more of $R^2$, $L^2$, $R^x$, $R^3$, $R^{10}$, $R^{12}$, $R^{13}$, and $R^{14}$ may together form a ring.

In some instances, any one or more of $R^{10}$, $R^{11}$, $R^{12}$, $R^{13}$, or $R^{14}$ is an optionally substituted ring system having the formula:

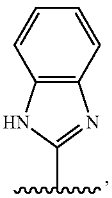, 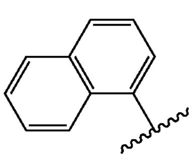, 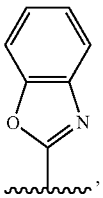, 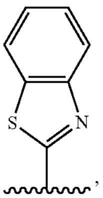,

-continued

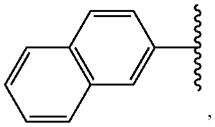, 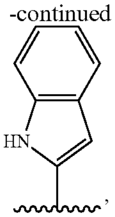, 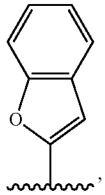, 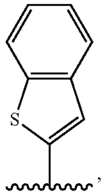,

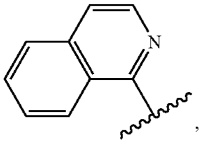, 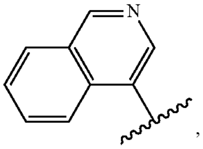,

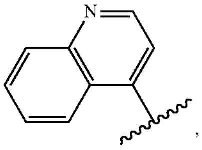, 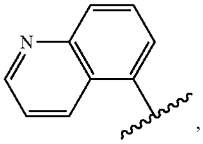,

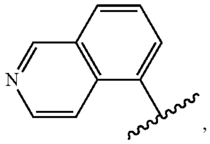, 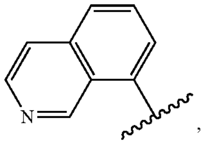,

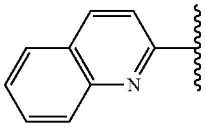, 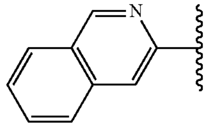,

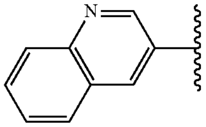, 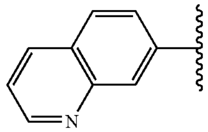,

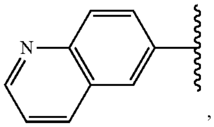, 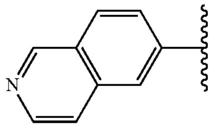,

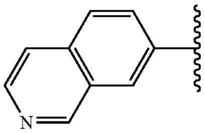, 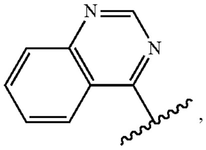,

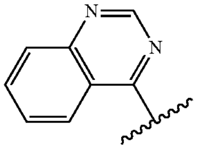, 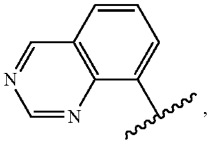,

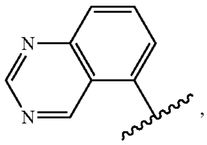, 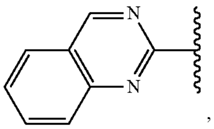,

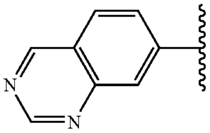, 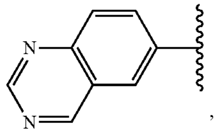,

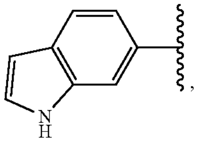, 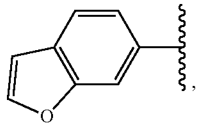,

-continued

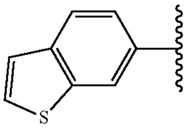, 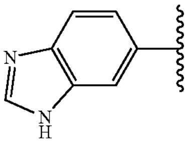,

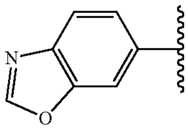, 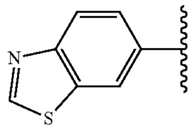, 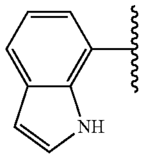,

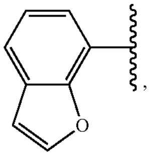, 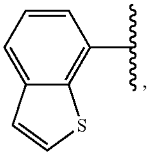, 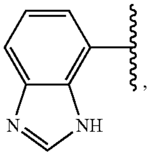,

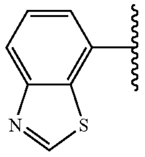, 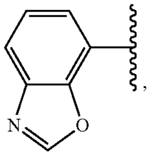, 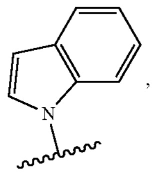, or

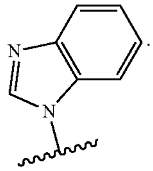.

Although the above ring systems are depicted as unsubstituted, in certain embodiments additional substituents, as defined above, may be present.

In certain preferred embodiments, $Q^1$ and $Q^2$ are each absent, while in other embodiments, $Q^1$ is absent, and $Q^2$ is a group having the formula —($CR^{q2}R^{q2'}$)—, wherein $R^{q2}$ is hydrogen and $R^{q2'}$ is hydrogen, OH, or $C_{1-6}$alkyl. In some instances, $Q^2$ is absent, and $Q^1$ is a group having the formula —($CR^{q1}R^{q1'}$)—, wherein $R^{q1}$ is hydrogen and $R^{q1'}$ is hydrogen, OH, or $C_{1-6}$alkyl.

A preferred group of compounds includes those in which both $R^1$ and $R^2$ are hydrogen, and other preferred compounds include those in which $R^1$ and $R^2$ are each hydrogen, and Z is oxygen.

In other embodiments, Z is $NR^3$, and $R^3$ may form a ring with one or more of $L^2$ or $Ar^2$. For instance, compounds having the formula:

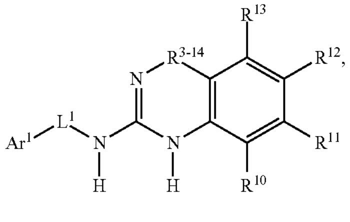, wherein $Ar^1$, $L^2$, $R^{10}$, $R^{11}$, $R^{12}$, and $R^{13}$ are as defined above, and $R^{3-14}$ is a chemical bond, O, $CH_2$ or C(O).

In some embodiments are provided compounds having the formula:

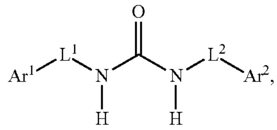, wherein $Ar^1$, $L^1$, $L^2$, and $Ar^2$ have the aforementioned meanings. In certain embodiments, $L^2$ is absent and $L^1$ is an optionally substituted $C_{1-8}$alkyl group:

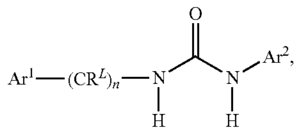, wherein $Ar^1$ and $Ar^2$ have the aforementioned meanings, n is an integer from 1-8, $R^L$ is in each case independently selected from $R^{La}$, $OR^{La}$, $N(R^{La})_2$, $SO_2R^{La}$, $SO_2N(R^{La})_2$, $C(O)R^{La}$; $C(O)OR^{La}$, $OC(O)R^{La}$; $C(O)N(R^{La})_2$, $N(R^{La})C(O)R^{La}$, $OC(O)N(R^{La})_2$, $N(R^{La})C(O)N(R^{La})_2$, wherein $R^{La}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl, wherein any two or more of $Ar^1$, $R^L$ and $Ar^2$ may together form a ring. In some embodiments, the compounds can have the formula:

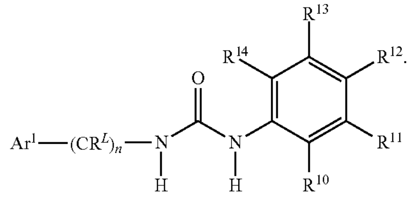.

In some cases, $Ar^2$ can be a monosubstituted aryl ring such as:

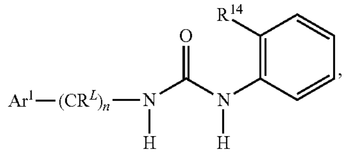,

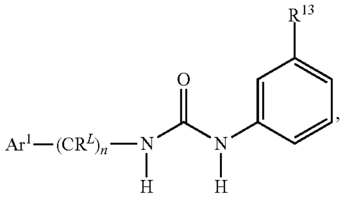, or

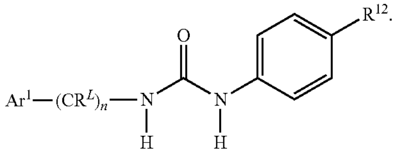.

In certain embodiments, $Ar^2$ can be a disubstituted aryl ring

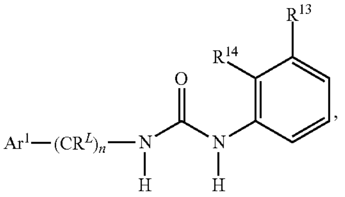

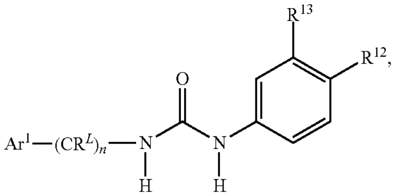

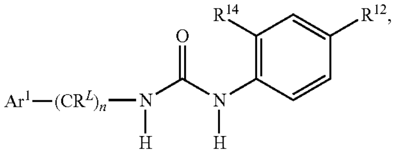

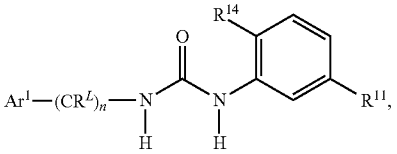

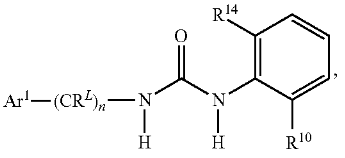

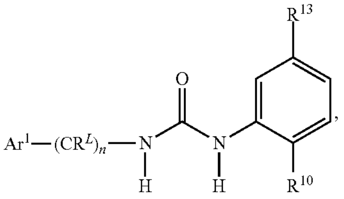

or

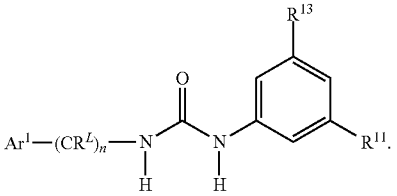

In certain embodiments, Z can be $NR^3$, and $R^3$ can form a ring with $Ar^2$. Exemplary embodiments include compounds having $L^2$ (as defined above) and compounds in which $L^2$ is absent:

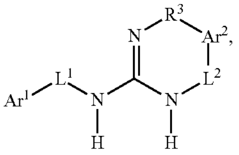

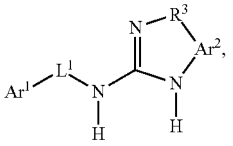

-continued

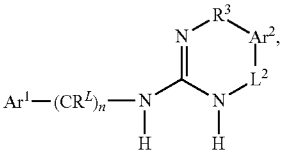

or

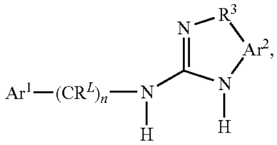

wherein $Ar^1$, $L^1$, $L^2$, n, $R^L$, $Ar^2$ and $R^3$ have the meanings given above. Also provided are compounds in which $R^3$ and $Ar^2$ form a ring, and $Ar^2$ is an aryl ring:

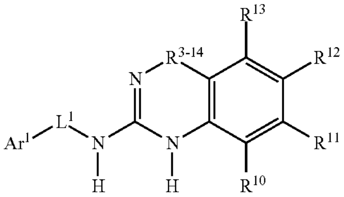

or

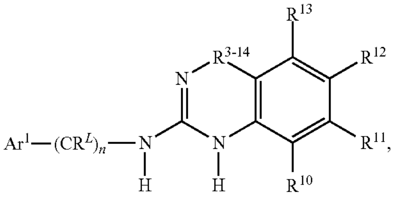

wherein $R^{3-14}$ is selected from a chemical bond, $C_{1-4}$alkyl, O, or C(O), and $Ar^1$, $L^1$, $R^L$, n, $R^{10}$, $R^{11}$, $R^{12}$, and $R^{13}$ have the aforementioned meanings.

In some embodiments, the disruptor compounds can have the formula:

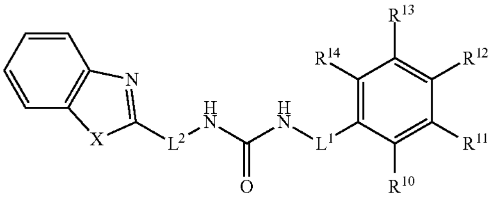

or

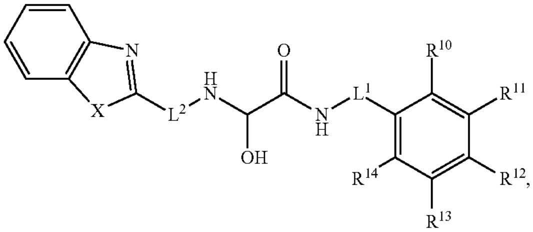

wherein X is O or NH, and $L^2$, $L^1$, $R^{10}$, $R^{11}$, $R^{12}$, $R^{13}$, and $R^{14}$ are as defined above. In certain embodiments, $R^{10}$, $R^{11}$, and $R^{14}$ are each hydrogen, and $R^{12}$ and $R^{13}$ are each $C_{1-4}$alkoxy, and may optionally together form a ring. In some instance, $L^2$ can be absent, aryl, $C_{1-3}$alkylene, especially methylene ($CH_2$), and heterocyclyl. Preferred $L^1$ groups include $C_{1-3}$alkylene, especially methylene ($CH_2$). In certain embodiments, the disruptor compounds can have the formula:

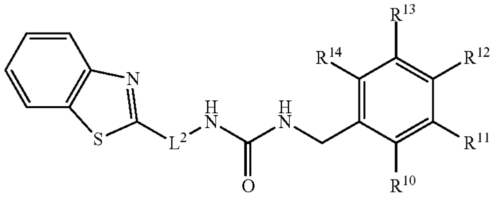

or

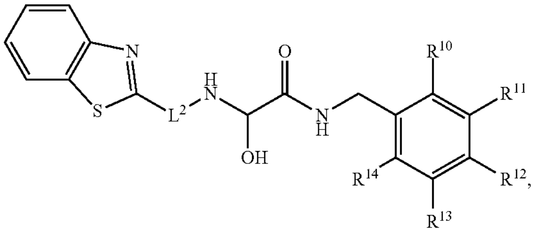

Preferred $C_{1-4}$alkoxy groups include methoxy, and preferred ring systems include dioxin (six member ring) and dioxolyl (five membered ring) systems. In certain cases, the disruptor compound can be:

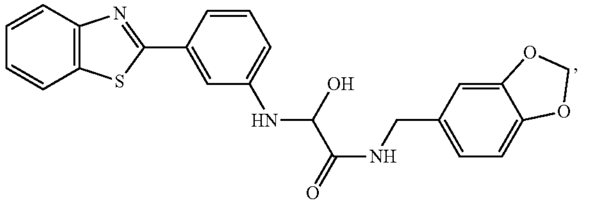

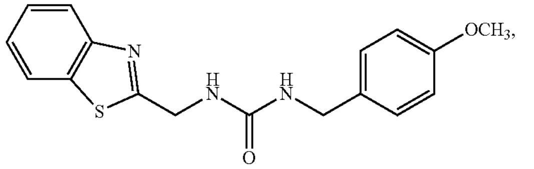

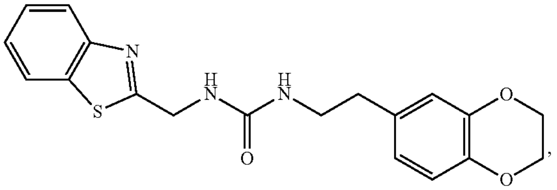

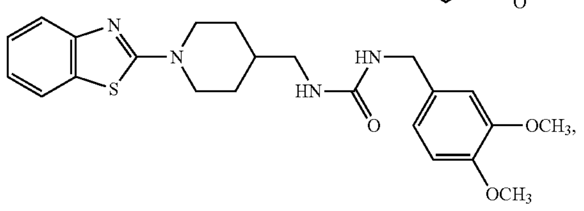

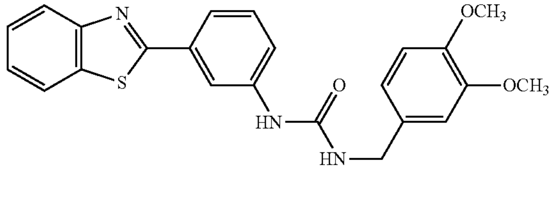

The disrupter compounds disclosed herein may be used to treat neurological damage, for instance damage to neurons, especially neurons in the central nervous system. Neuronal damage can be caused by a variety of conditions and events, such as ischemic stroke, hemorrhagic stroke or brain injury, such as traumatic brain injury. The disrupter compounds disclosed herein may be used to treat a variety of neurodegenerative diseases. Neurodegenerative diseases are typically characterized by the progressive loss of structure or function of neurons, such as neurons within the cerebral cortex, basal ganglia, cerebellum, brain stem or motor systems. Neurodegenerative disorders include, but are not limited to, Alzheimer's disease, Parkinson's disease, Huntington's disease, ALS, multiple sclerosis, Lewy body dementia, vascular dementia, progressive supranuclear palsy, corticobasal degeneration, multiple system atrophy and frontotemporal dementia.

Methods of administering therapeutic compounds are well known in the art. In some embodiments of the disclosed methods, the disclosed compounds are administered to a subject for the treatment of cerebral ischemia (for instance caused by cardiac arrest), stroke (such as ischemic stroke or hemorrhagic stroke), CNS trauma/injury, traumatic brain injury, a neurodegenerative disease, or any other condition associated with neuronal damage and/or neuronal cell death. When administering such compounds, one must consider the appropriate target site based on the disease to be treated. If the site of action is the central nervous system, the compound must be able to cross the blood brain barrier (BBB), injected intrathecally, or be delivered directly to the target site in the brain.

In some embodiments, the disclosed compounds may be provided in the form of a pharmaceutical composition such as but not limited to, unit dosage forms including tablets, capsules (filled with powders, pellets, beads, mini-tablets, pills, micro-pellets, small tablet units, multiple unit pellet systems (MUPS), disintegrating tablets, dispersible tablets, granules, and microspheres, multiparticulates), sachets (filled with powders, pellets, beads, mini-tablets, pills, micro-pellets, small tablet units, MUPS, disintegrating tablets, dispersible tablets, granules, and microspheres, multiparticulates), powders for reconstitution and sprinkles, transdermal patches, however, other dosage forms such as controlled release formulations, lyophilized formulations, modified release formulations, delayed release formulations, extended release formulations, pulsatile release formulations, dual release formulations and the like. Liquid and semisolid dosage forms (liquids, suspensions, solutions, dispersions, ointments, creams, emulsions, microemulsions, sprays, patches, spot-on), parenteral, topical, inhalation, buccal, nasal etc. may also be envisaged under the ambit of the invention.

Suitable excipients may be used for formulating the dosage form according to the present invention such as, but not limited to, surface stabilizers or surfactants, viscosity modifying agents, polymers including extended release polymers, stabilizers, disintegrants or super disintegrants, diluents, plasticizers, binders, glidants, lubricants, sweeteners, flavoring agents, anti-caking agents, opacifiers, antimicrobial agents, antifoaming agents, emulsifiers, buffering agents, coloring agents, carriers, fillers, anti-adherents, solvents, taste-masking agents, preservatives, antioxidants, texture enhancers, channeling agents, coating agents or combinations thereof.

In some embodiments, the disrupter compounds are administered by direct infusion into the brain, such as by intracerebroventricular (ICV) injection/infusion, intrastriatal injection, intranigral injection, intracerebral injection, infusion into the putamen, intrathecal infusion (such as by using an implanted pump) or by subcutaneous injection. Intranasal administration of compounds also leads to delivery to the CNS. Thus, in some examples, the disrupter compound is administered intranasally The compounds disclosed herein may be prepared using conventional urea forming chemistries. Unsymmetrical ureas may be prepared using a Curtius rearrangement, Lossen rearrangement, carbonylation of an azide in the presence of an amine, or sequential reaction of amines with biselectrophiles such as carbonyl di-imidazole or S,S-dimethyl dithiocarbonate.

EXAMPLES

The following examples are for the purpose of illustration of the invention only and are not intended to limit the scope of the present invention in any manner whatsoever.

Figure 7:
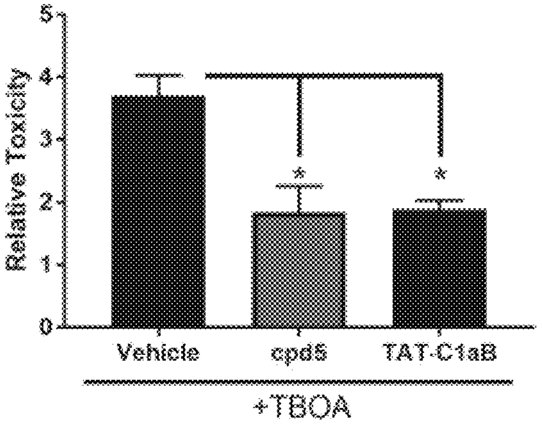
FIG. 7 depicts incubation of cortical culture neurons with 10 μM cpd5 was found to be highly neuroprotective against 75 μM TBOA-induced excitotoxicity. This protective effect was comparable with its peptide counterpart, TAT-C1aB (1 μM). (Vehicle vs cpd5 vs TAT-C1aB relative toxicity mean±SEM: 3.70±0.33 vs 1.84±0.42 vs 1.89±0.15; $*p<0.05$; Kruskal-Wallis non-parametric ANOVA; n=3-8).
Figure 8:
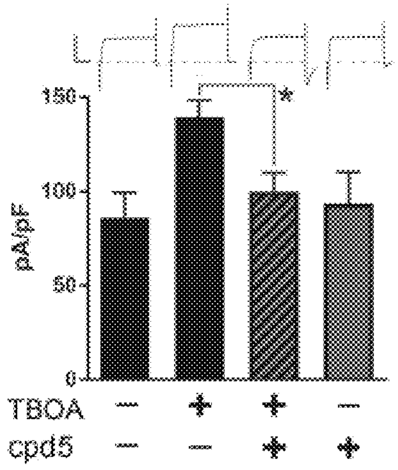
FIG. 8 depicts current density traces (top) and plots of the evoked delayed rectifier currents at +30 mV. The 50 μM TBOA-evoked increase in delayed rectifier current was significantly suppressed by the presence of 10 μM cpd5 (DMSO vs TBOA vs cpd5+TBOA: 85.92±13.53 vs 139.28±9.05 vs 100.12±,9.61 pA/pF; One-way ANOVA/Dunnett, $*p<0.05$). Scale bar indicates 100 pA/pF and 50 ms; n=10-12.
Figure 9:
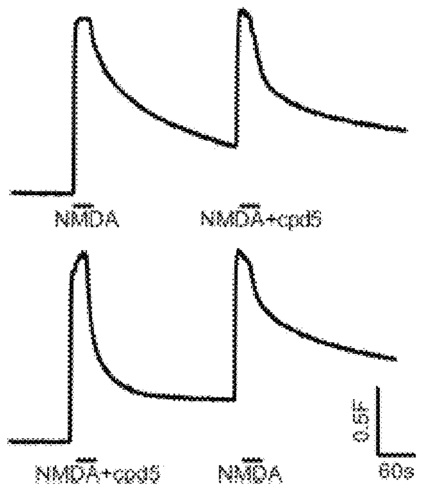
FIG. 9 depicts cpd5 (10 μM) did not inhibit NMDA-induced $Ca^{2+}$ responses in cultured cortical neurons (% Control±SEM, F-peak treated 101.26±1.47, AUC treated 104.67±1.98, n=4, 160 cells, $*p>0.05$; t-test). Responses shown are the average of 40 Fura-2 loaded cells in 2 separate coverslips. Four coverslips were utilized for our analysis.
Figure 10:
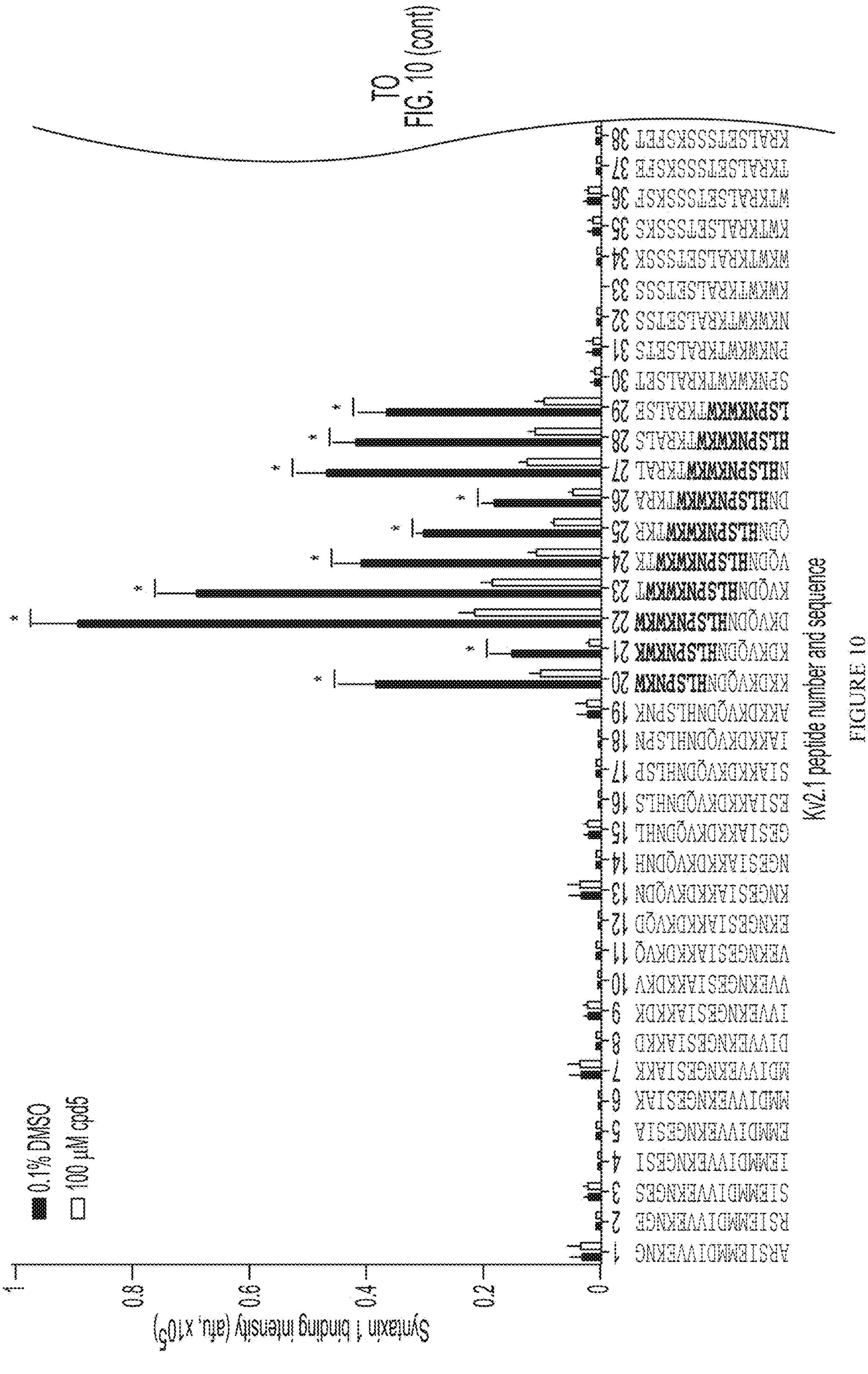
FIG. 10 depicts Far-Western assay of the proximal Kv2.1 C-terminus (C1a) region using 15 a. a. segments spanning residues Kv2.1 451-540, in overlapping 1 a. a. steps. Bar graph shows the summary (n=4) of syntaxin binding intensity in the presence of 100 μM cpd5 or 0.1% DMSO as vehicle control. The C1a binding sequence is highlighted in red.
Figure 10:
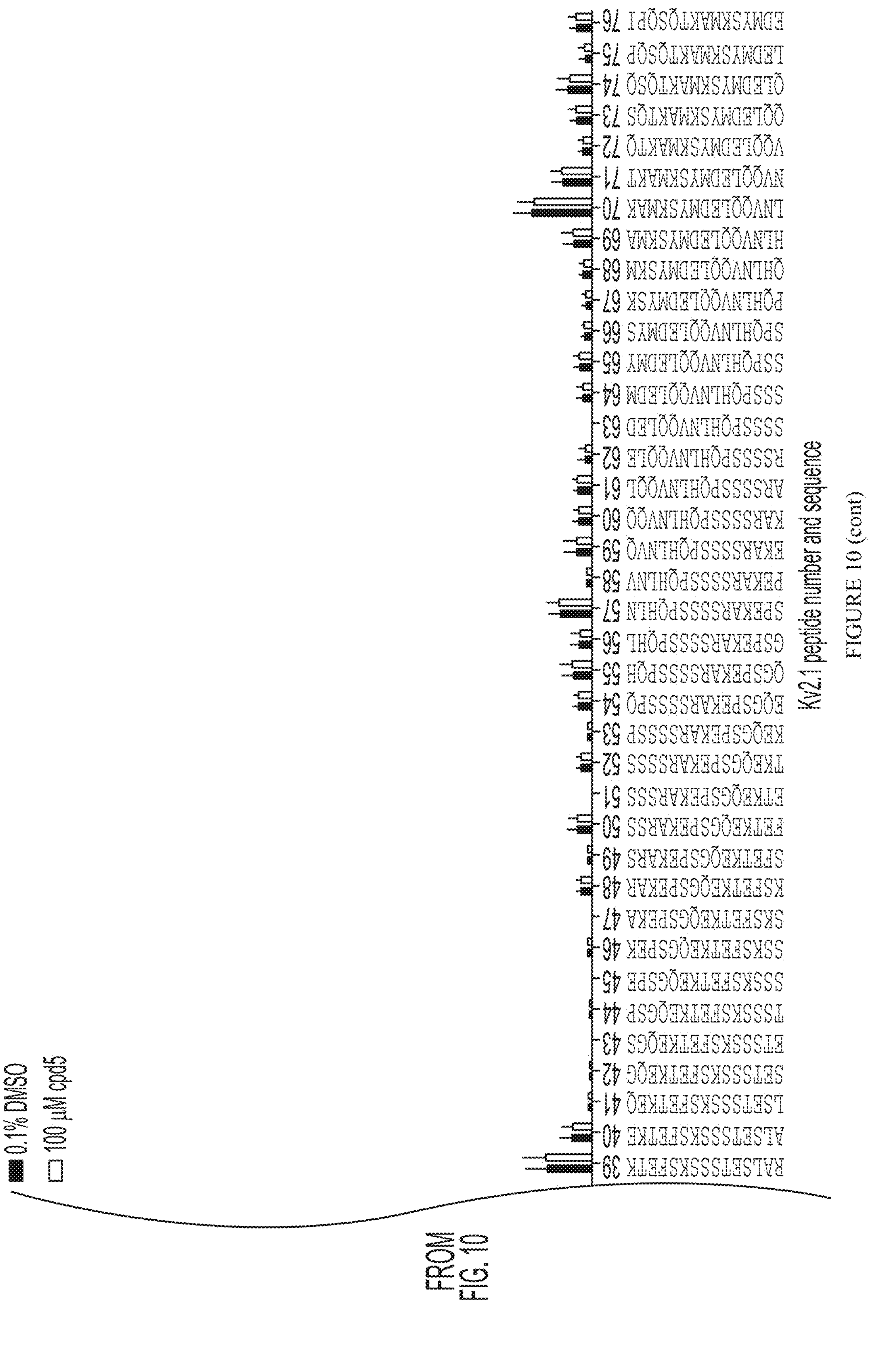
Figure 11:
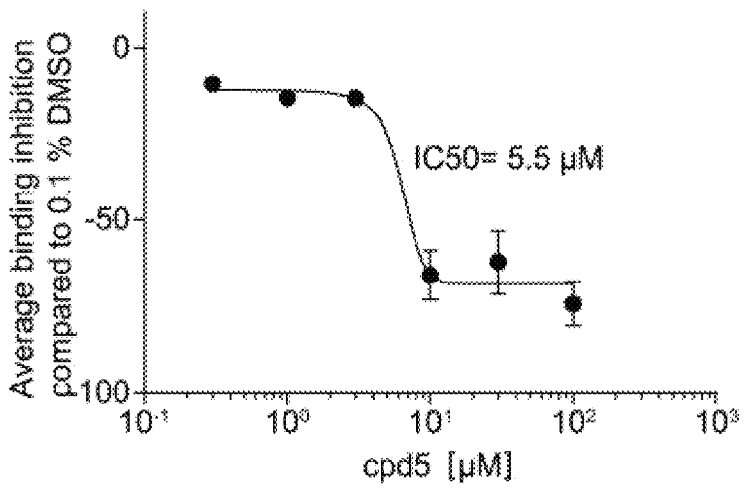
FIG. 11 depicts Concentration-dependent effect of cpd5 on syntaxin binding to the peptides 22-28 (containing the full C1aB19 domain) of the peptide array. Percent inhibition of syntaxin binding compared to 0.1% DMSO is plotted for various concentrations of cpd5. The data were fitted in GraphPad Prism with a log (inhibitor) vs normalized response with variable slope curve, which yielded an IC50 of 5.5 μM. $*p<0.05$, non-parametric Mann-Whitney for each peptide.
Figure 12:
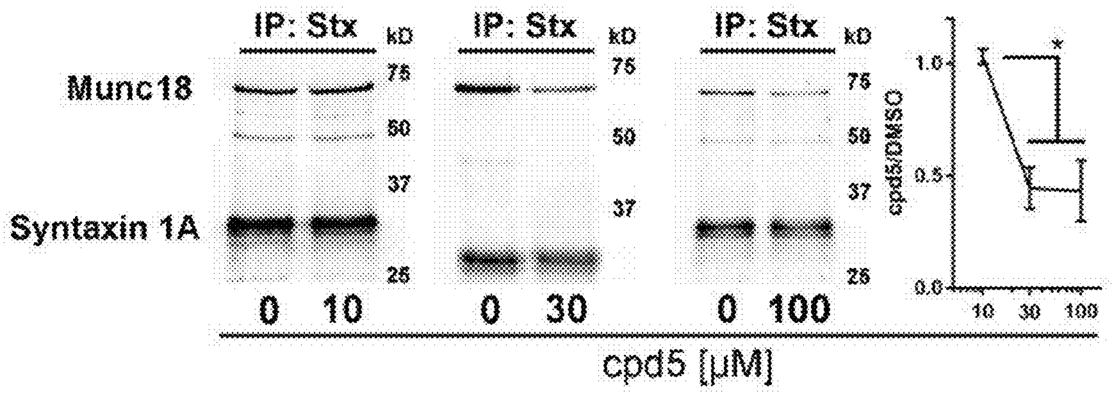
FIG. 12 depicts A graphical summary of coimmunoprecipitation experiments using HEK293 cells transfected with munc18 and syntaxin in the presence of 10, 30, or 100 μM cpd5. Cells incubated in either 30 or 100 μM cpd5 showed a significant displacement of munc18 from syntaxin. Cpd5 at the concentration that we have observed neuroprotection (10 μM) did not displace munc18 from syntaxin. One representative blot from each concentration is presented above. (From 10 to 100 μM: 1.032±0.034, 0.4459±0.09367, 0.4339±0.135, cpd5/DMSO mean±SEM; $*p<0.05$, Tukey's multiple comparisons, n=3 each).
Figure 13:
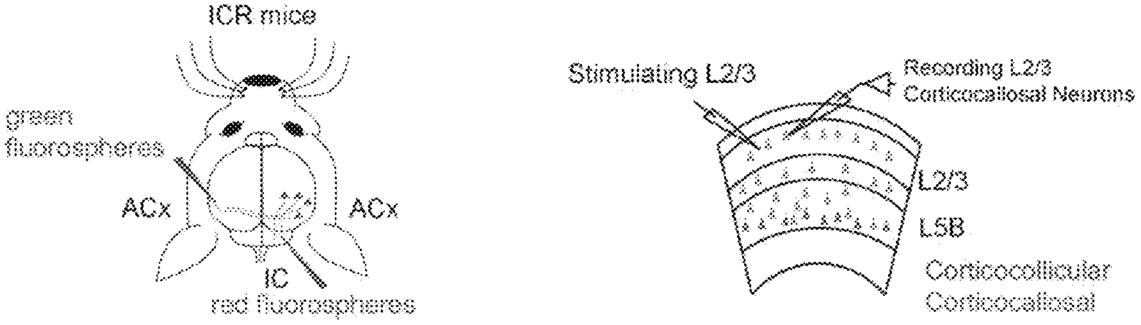
FIG. 13 depicts Left: Schematic of stereotaxic injections for labeling of corticocollicular and corticocallosal neurons with different flourospheres to identify select neurons in the auditory cortex for acute slice electrophysiology (left panel). The right panel depicts schematic illustrating slice electrophysiology experiment involving electrical stimulation of auditory cortex layer 2/3 while recording from adjacent labeled corticocallosal neurons.
Figure 14:
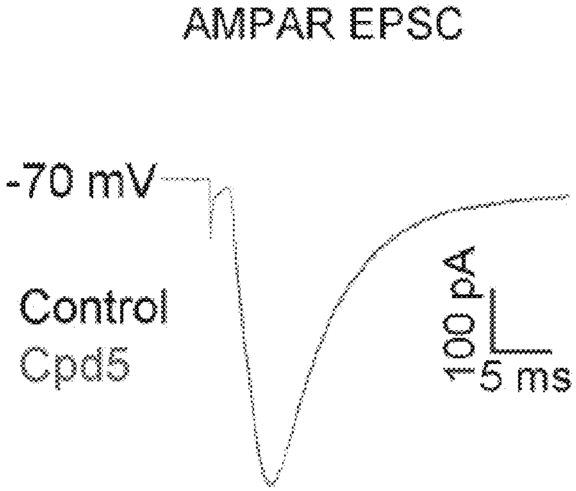
FIG. 14 depicts Representative traces of a layer 2/3 corticocallosal neuron AMPAR EPSCs evoked by electrical stimulation of adjacent layer 2/3 sites while incubated in control (black) and in 10 μM cpd5 (red).
Figure 15:
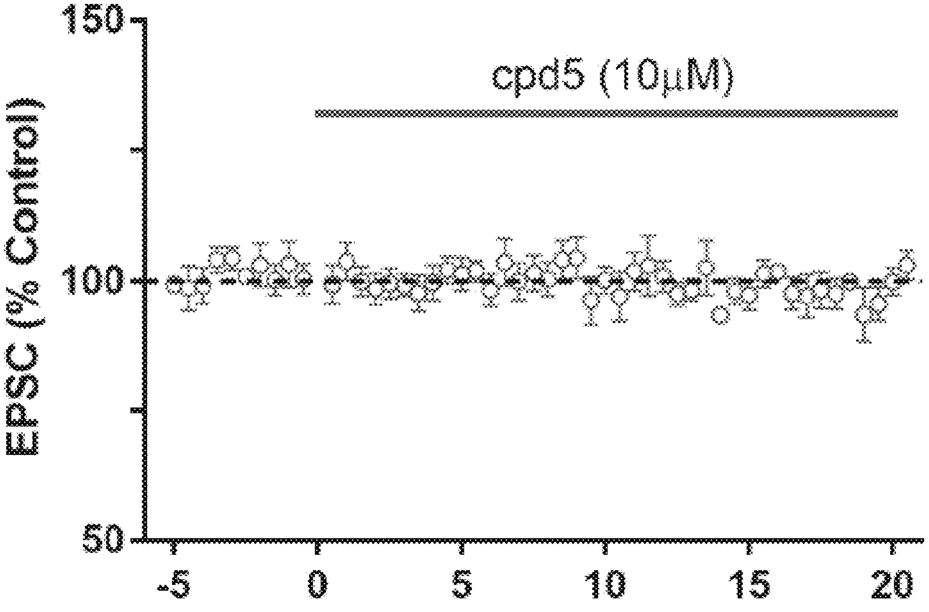
FIG. 15 depicts the time course of the average amplitude of AMPAR EPSCs before and after cpd5 treatment.
Figure 16:
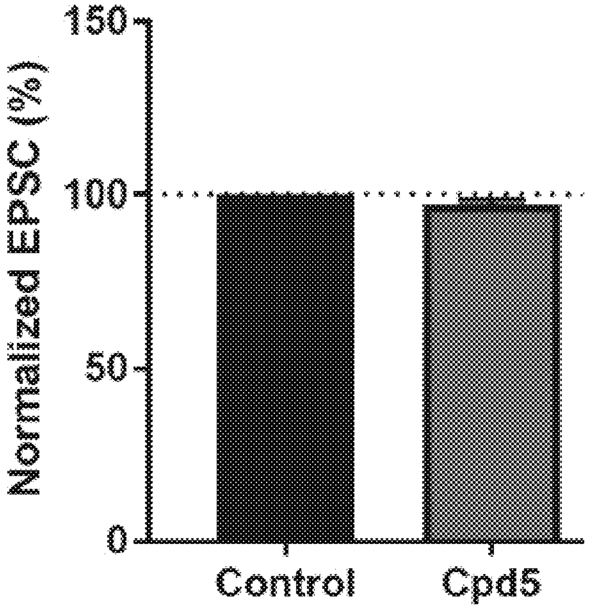
FIG. 16 depicts the average effect of cpd5 (red) on layer 2/3 corticocallosal neuron AMPAR EPSCs amplitudes, normalized to control (control vs. cpd5: 97.6±0.9%, p=0.153, paired t-test, n=4 cells from 4 mice).
Figure 17:
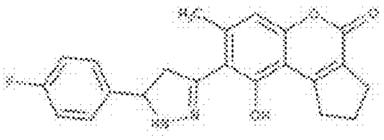
FIG. 17 depicts the chemical structure of certain tested compounds.
Figure 17:
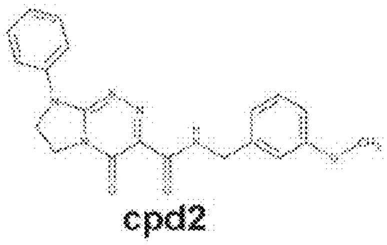
Figure 17:
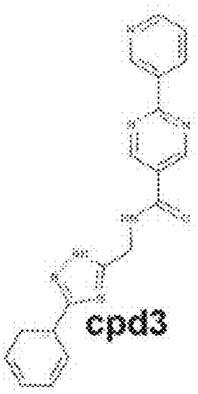
Figure 17:
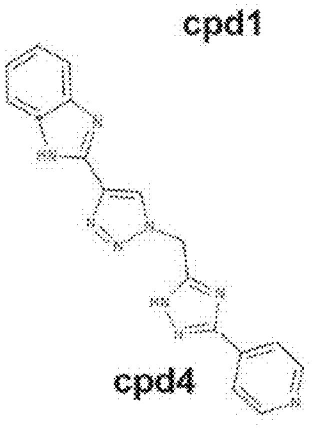
Figure 17:
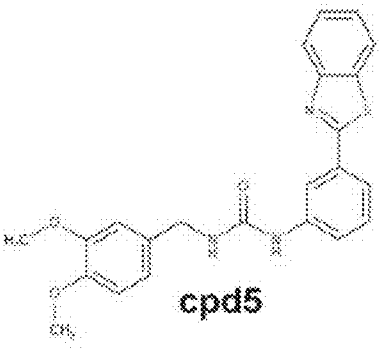
Figure 17:
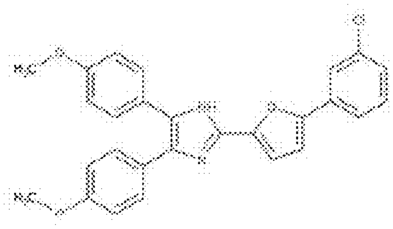
Figure 18:
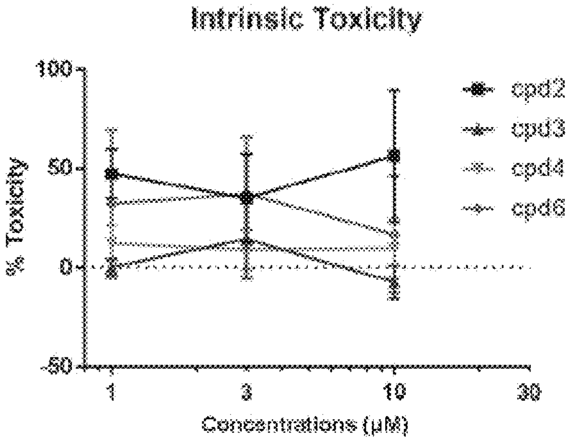
FIG. 18 depicts the LDH toxicity assay screening of four small molecules evaluated for innate toxicity to primary rat cortical neuron cultures.
Figure 19:
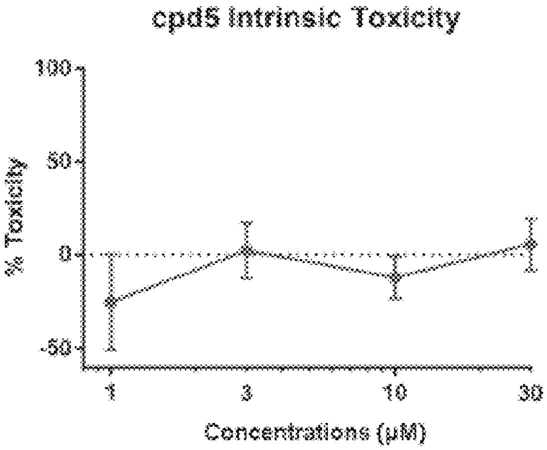
FIG. 19 depicts the LDH toxicity assay screening of the lead compound cpd5 in primary cortical neuron cultures found no innate toxicity of up to 30 μM for 24 hr.
Figure 20:
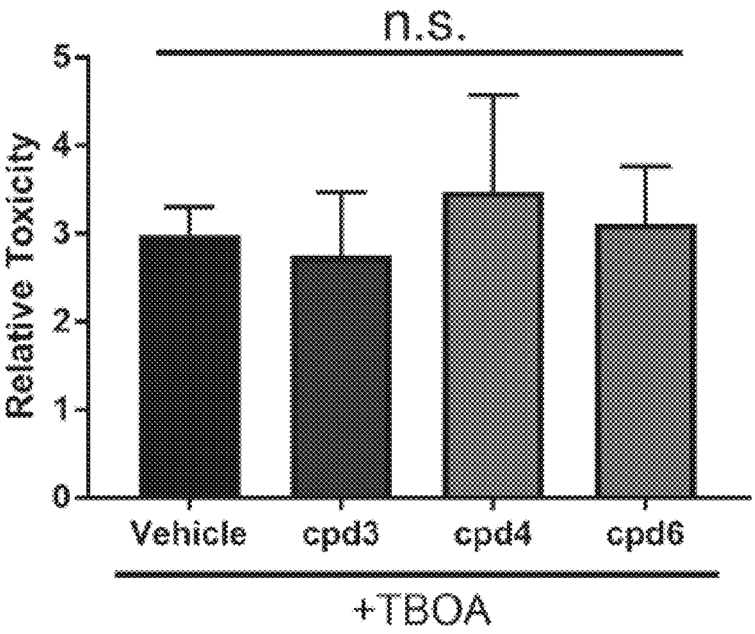
FIG. 20 depicts the incubation of cortical culture neurons with 10 μM cpd3, cpd4, or cpd6 provided no neuroprotection against 75 μM TBOA-induced excitoxicity (Vehicle vs cpd3 vs cpd4 vs cpd6 relative toxicity mean±SEM: 2.99±0.32 vs 2.75±0.72 vs 3.48±1.1 vs 3.12±0.65; Kruskal-Wallis non-parametric ANOVA; n=3-9).
Figure 21:
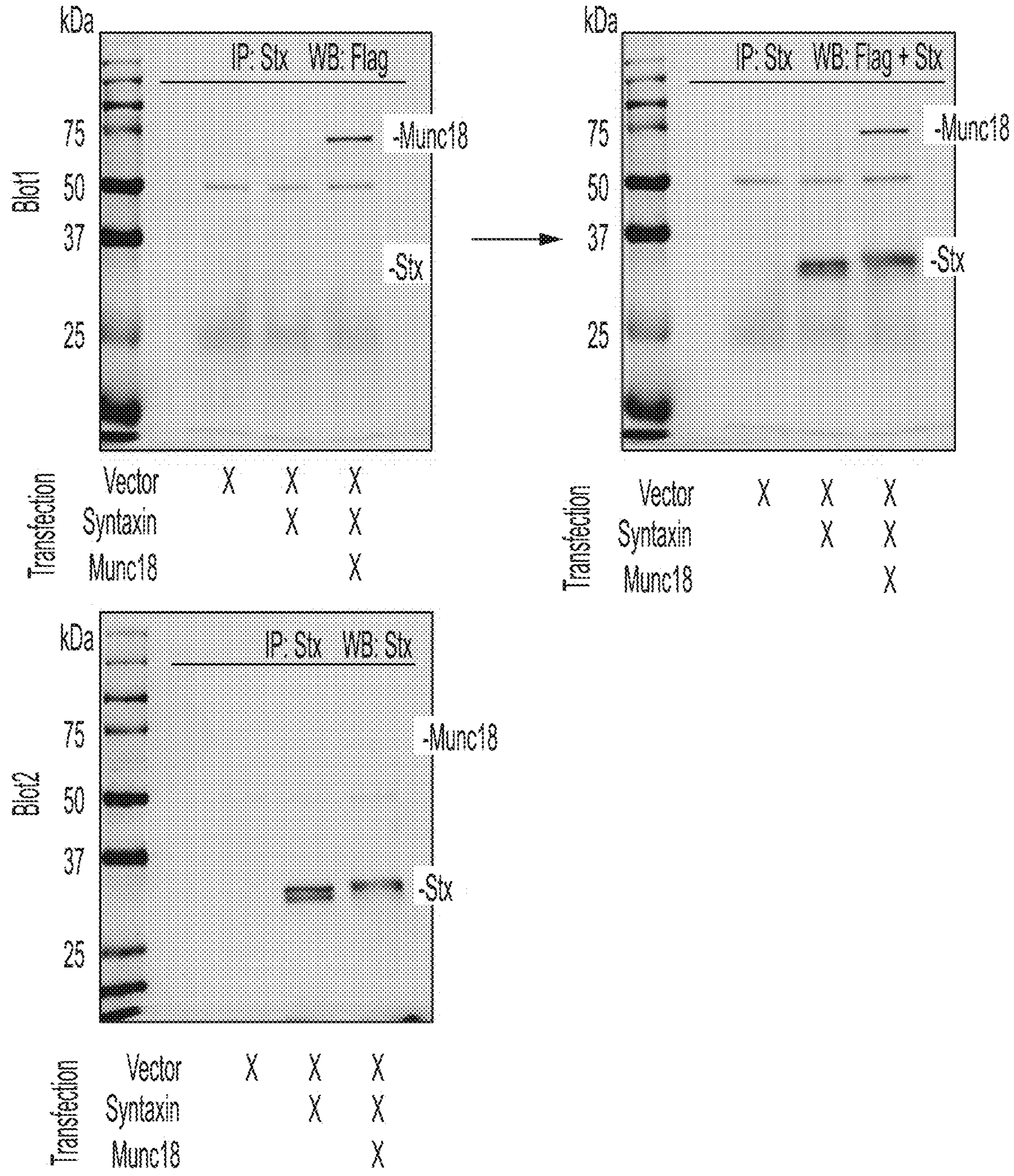
FIG. 21 Top: Confirmation that the 68 kDa band to be munc18 and the 33 kDa band to be syntaxin 1A by observing that they do not appear in samples without prior transfection with appropriate plasmids in HEK cells. The munc18 antibody does not detect the syntaxin band. In the first blot, munc18 was probed first, followed by syntaxin. Bottom: In a separate run of the same sample, the specificity of the syntaxin antibody was confirmed by probing with the syntaxin antibody only, observing relatively lack of signal at the MW for munc18. The co-transfection of munc18 with syntaxin appears to induce a formation of a higher molecular weight syntaxin species. Bands at 50 and 25 kDa are the heavy and light chain of the pulldown antibody, respectively.
Figure 22:
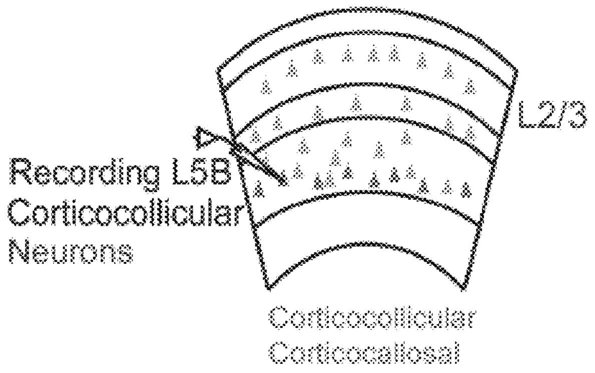
FIG. 22 depicts Schematic illustrating slice electrophysiology experiment evaluating the intrinsic properties of L5B corticocollicular neurons after retrograde labeling.
Figure 23:
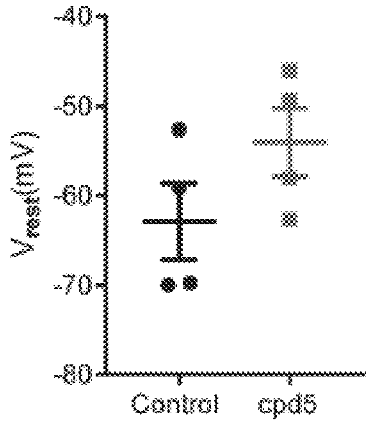
FIG. 23 depicts an evaluation of subthreshold intrinsic properties found a lack of significant effect of cpd5 incubation on resting membrane potential.
Figure 24:
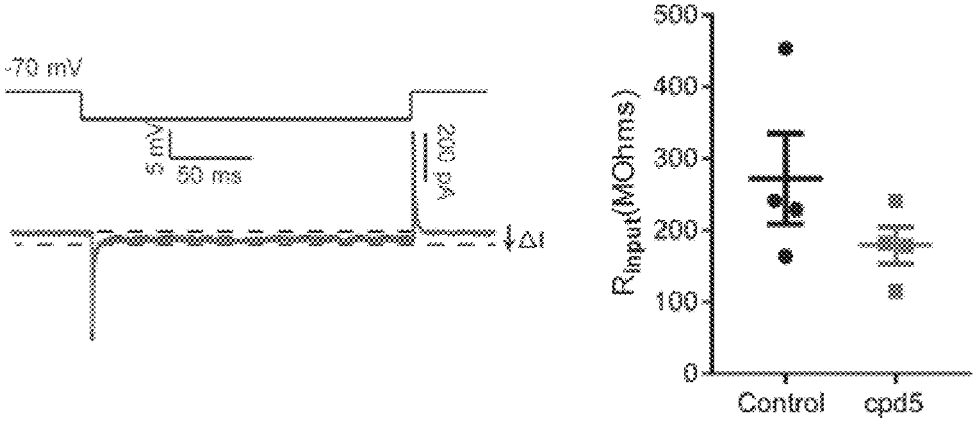
FIG. 24 depicts an evaluation of subthreshold intrinsic properties found a lack of significant effect of cpd5 incubation on input resistance.
Figure 25:
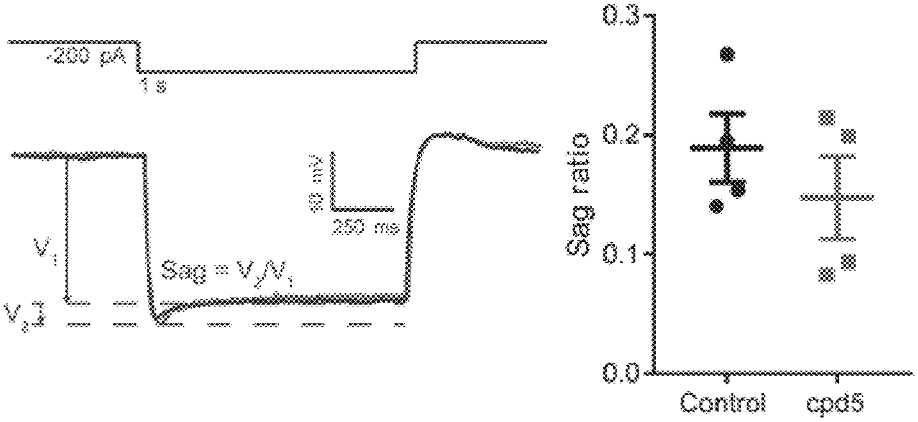
FIG. 25 depicts an evaluation of subthreshold intrinsic properties found a lack of significant effect of cpd5 incubation on sag ratio ($V_2/V_1$).
Figure 26:
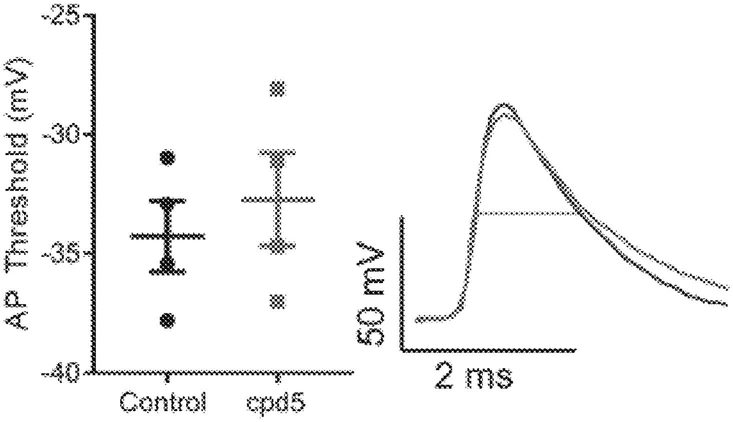
FIG. 26 depicts An evaluation of evoked properties also found no significant effect of cpd5 incubation on action potential threshold. Available representative traces are provided for each experiment. Each neuron is evaluated before and after 10 min incubation in 10 μM cpd5 (Paired t-test; for firing rates, 2-way ANOVA; n=4 cells from 4 mice).
Figure 27:
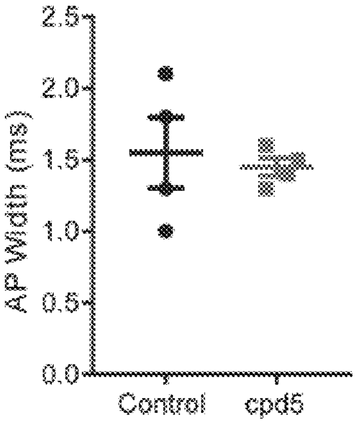
FIG. 27 depicts An evaluation of evoked properties also found no significant effect of cpd5 incubation on width. Available representative traces are provided for each experiment. Each neuron is evaluated before and after 10 min incubation in 10 μM cpd5 (Paired t-test; for firing rates, 2-way ANOVA; n=4 cells from 4 mice).
Figure 28:
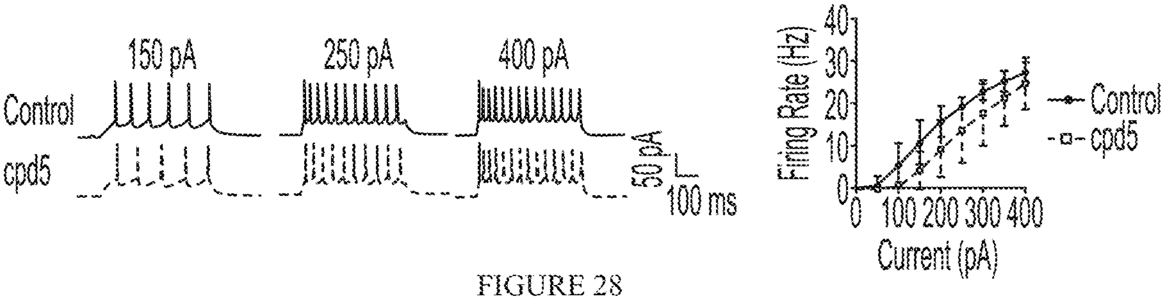
FIG. 28 depicts An evaluation of evoked properties also found no significant effect of cpd5 incubation on firing rate. Available representative traces are provided for each experiment. Each neuron is evaluated before and after 10 min incubation in 10 μM cpd5 (Paired t-test; for firing rates, 2-way ANOVA; n=4 cells from 4 mice).

The compound 3-[3-(1,3-benzothiazol-2-yl)phenyl]-1-[(3,4-dimethoxyphenyl) methyl]urea), designated herein as Cpd5, was evaluated in vitro for innate toxicity and then for neuroprotective actions in rat primary culture cortical neurons. No neurotoxicity was observed at concentrations as high as 30 μM (FIG. 7). We next examined whether Cpd5 would provide neuroprotection against overnight applications of threo-beta-Benzyloxyaspartate (TBOA; 60 μM), a relatively non-selective glutamate uptake inhibitor (Shimamoto et al., 1998) that induces gradual, NMDA receptor-mediated excitotoxicity in our cultures accompanied by a pronounced increase in $K^+$ currents (Yeh et al., 2017). We found that pre-loading (1 hr) and co-incubation with 10 μM Cpd5 significantly diminished TBOA toxicity, an effect nearly identical to the actions of 1 μM TAT-C1aB treatment.

Figure 2:
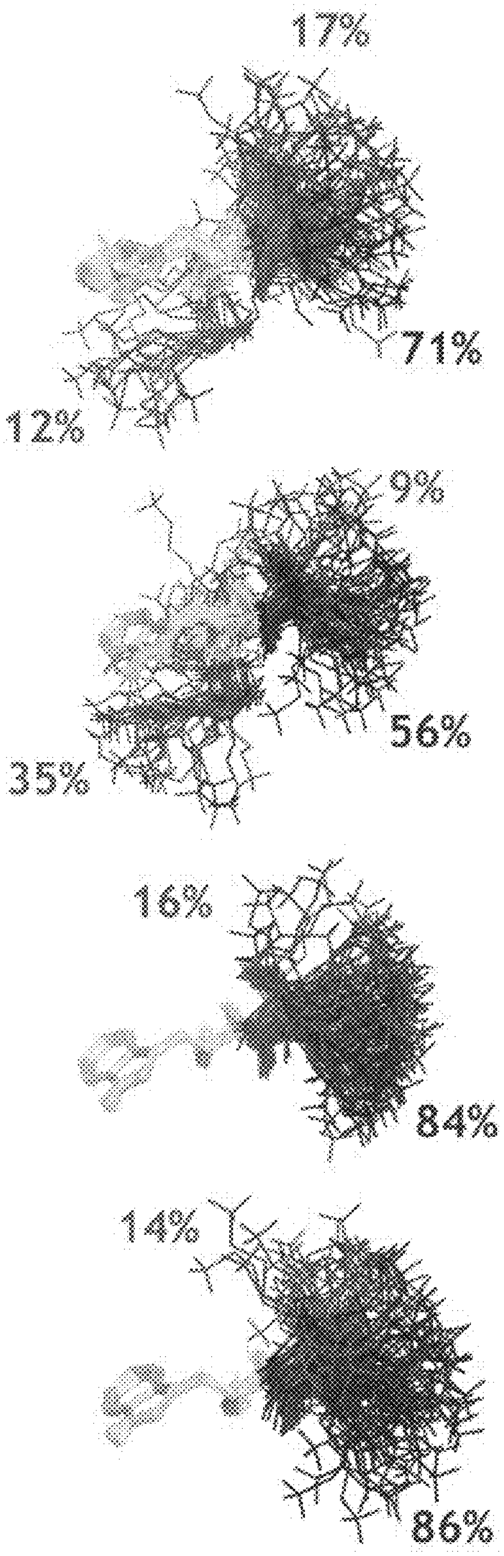
FIG. 2 depicts first KW motif from 100 snapshots of the corresponding peptides every 4 ns (after 100 ns of equilibration), snapshots were aligned on the W (grey). Strong binding peptides have W solvent exposed and ready to make contact with interacting surface, this is disrupted in peptides of the first two rows with compromised second KW motif.

A hallmark of Kv2.1-facilitated neuronal cell death is the accompanying dramatic increase in delayed rectifier $K^+$ currents as the result of syntaxin-dependent de novo Kv2.1 channel plasma membrane insertion (Pal et al., 2006). Plasmid-mediated overexpression of the C1a region or the use of the TAT-C1aB peptide can prevent the Kv2.1-mediated current surge (McCord et al., 2014; Yeh et al, 2017). To determine whether Cpd5 can achieve similar inhibition of current enhancement, we carried out whole cell patch clamp recordings of rat primary cortical culture neurons after co-incubation with TBOA (50 μM for 2 hr followed by 2 hr resting period). In strong agreement with our neuroprotection assays, we found that Cpd5 (10 μM) pre-loading (1 hr) and co-treatment with TBOA effectively suppressed the post-injury enhancement of delayed rectifier $K^+$ currents in neurons to levels comparable to uninjured neurons (FIG. 2C). Most importantly, we found no significant effects of Cpd5 incubation alone on basal $K^+$ current densities (FIG. 2C), strongly suggesting that pre-existing membrane-bound channels and the normal trafficking of the channel during the 5 hours total of Cpd5 incubation are unaffected by this compound. This is consistent with previous findings in cells expressing the C1a region or treated with TAT-C1aB (McCord et al., 2014; Yeh et al., 2017).

Because NMDA receptors mediate the neurotoxicity elicited by glutamate-uptake inhibitors (Blitzblau et al., 1996), it was necessary to ensure Cpd5 did not inhibit $Ca^{2+}$ responses mediated by these receptors, a major component of acute excitotoxicity (Sattler & Tymianski, 2001). We thus performed Fura-2 ratiometric $Ca^{2+}$ imaging in rat cortical culture neurons during NMDA (30 μM with 10 μM glycine) exposure, noting a lack of any effect of concurrently-administrated Cpd5 (10 μM) on NMDA-evoked $Ca^{2+}$ responses (FIG. 2D). This strongly indicates that the aforementioned neuroprotective actions of Cpd5 likely did not occur as a result of direct interference with the upstream components of the excitotoxic cascade. Rather, these findings are evidence that Cpd5, like TAT-C1aB, provide neuroprotection against TBOA-induced excitotoxicity specifically by preventing the expression of enhanced Kv2.1-mediated $K^+$ currents.

Figure 3:
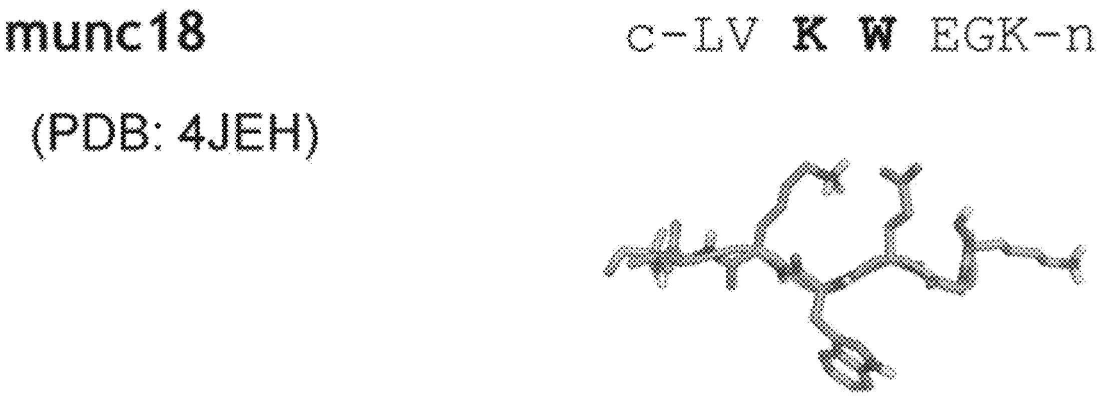
FIG. 3 depicts the binding region of syntaxin (teal surface) and munc-18 (green surface) from PDB 3C98. Zoom region of munc-18 N-terminal motif 25-31 interaction with syntaxin, stacking of munc-18 W28 and syntaxin F34 is shown. Note that this peptide is only a very small, peripheral component of the full binding interface of munc-18 and syntaxin.
Figure 4:
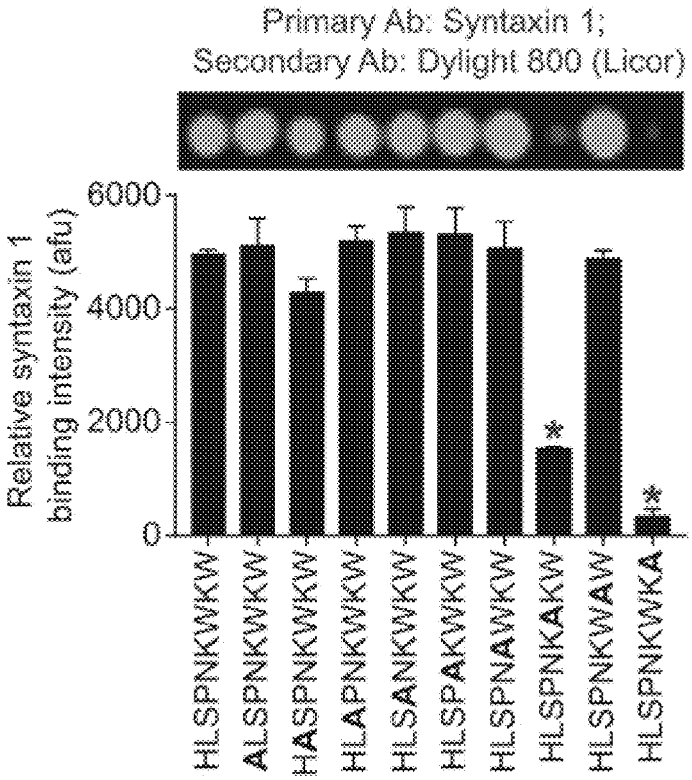
FIG. 4 depicts far-western assay of the C1aB sequence with sequential alanine substitutions, one residue at a time. Tryptophan to alanine-substituted peptides had significantly less syntaxin binding than the parent peptide (*$p<0.05$; ANOVA/Dunnett). Results indicate mean±SEM of signal intensity in 4 independent assays.

To confirm the molecular mechanism of Cpd5, we first performed further DMS analysis, revealing that the predicted pose of Cpd5 bound to syntaxin does indeed recapitulate the aromatic ring-stacking of C1aB KW with syntaxin F34, as well as three hydrogen bonds coordinating the water molecules (FIG. 3A). In a far Western assay (Yeh et al., 2017), we biochemically confirmed that Cpd5 (100 μM) significantly reduced the binding between syntaxin and Kv2.1 peptides containing the C1aB region previously reported (Red sequences, FIG. 3B; (Yeh et al., 2017)). At peak values, the presence of Cpd5 reduced Kv2.1 peptides binding to syntaxin by up to 60% (FIG. 3C). Next, we performed a co-immunoprecipitation assay of syntaxin and munc-18 in transfected HEK293 cells incubated in the presence or absence of Cpd5. We found that Cpd5 (100 μM) robustly disrupts the binding between munc-18 and syntaxin (FIG. 4B). Of note, at the neuroprotective concentration of 10 μM, Cpd5 did not displace munc-18 from syntaxin (FIG. 4C). Together, these results strongly suggest that the observed neuroprotective actions of Cpd5 are due to its binding to syntaxin F34, thus effectively preventing the interaction of Kv2.1 with the SNARE protein.

Figure 5:
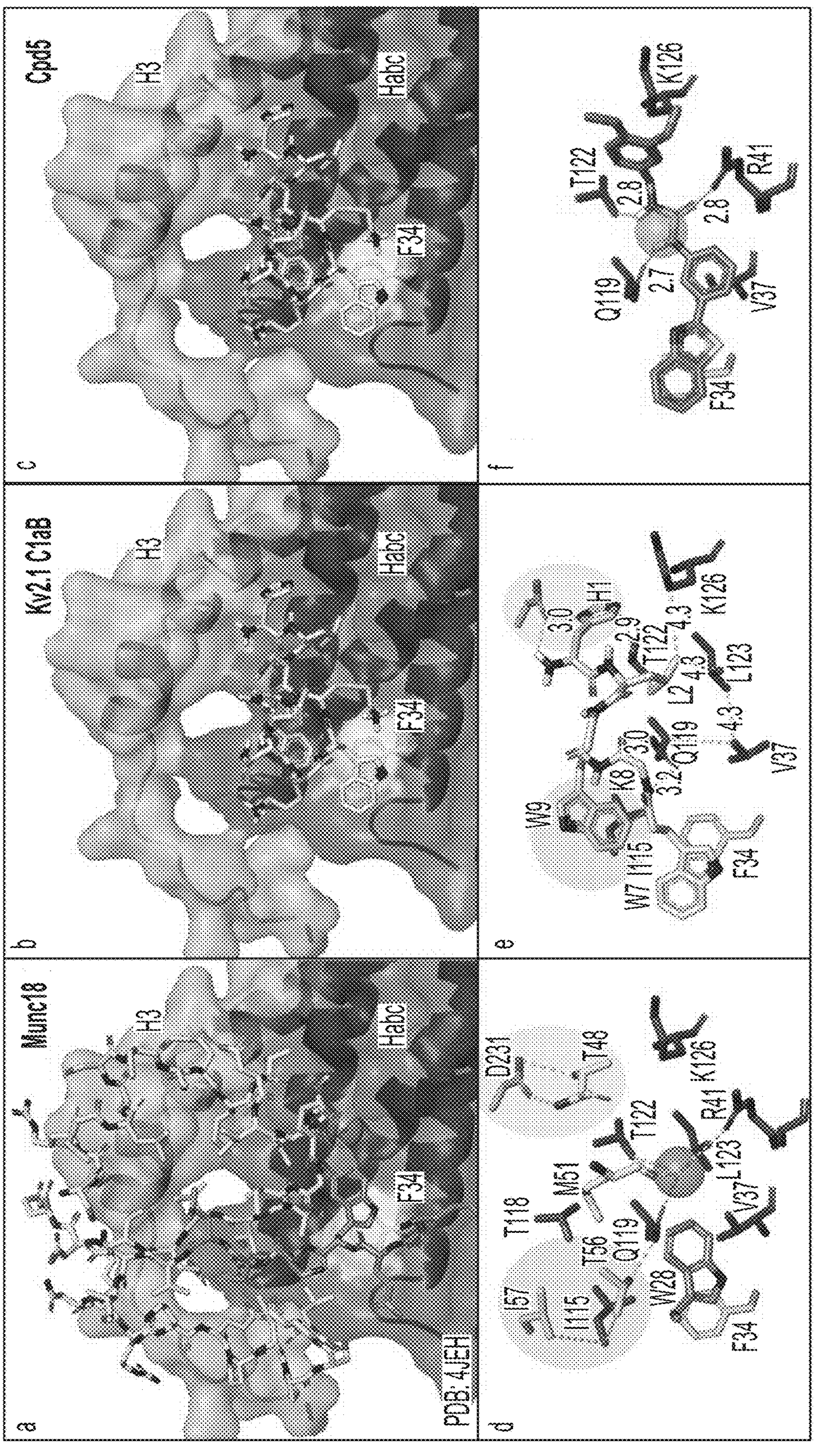
FIG. 5 depicts docked C1aB peptide and cpd5 recapitulates interactions of munc18/syntaxin co-crystal. Closed form of syntaxin from munc18 co-crystal (PDB 4JEH) is shown in green and cyan (surface/sticks) corresponding to the Habc and the H3 domains, respectively. Syntaxin F34 is shown in magenta to emphasize specific aromatic stacking interaction in all panels. a, Partial view of munc18/syntaxin co-crystal. Orange sticks show same munc18 peptide as in FIG. 1*c*, other munc18 residues making favorable interactions are shown in yellow sticks. Red sphere highlights fully coordinated crystal water. b, Unbiased docking model of C1aB/syntaxin. c, Docking model of cpd5/syntaxin. Water molecule is shown as a guide-to-the-eye to highlight the overlap with the urea moeity of cpd5. d, Highlighted intermolecular interactions of munc18/syntaxin that are recapitulated in e, detailed view of interactions between docked pose of C1aB and syntaxin. Specifically, munc18 W28 aromatic stacking is mimicked by C1aB W7; hydrophobic interactions between munc18 I57 and T56 and syntaxin I115 are mirrored by C1aB W9 (blue shade); hydrogen bond between munc18 T48 and syntaxin D231 is reproduced by FU in C1aB (red shade), f, Interactions between cpd5 and syntaxin. Namely, benzothiazole ring forms stacking interaction with F34, with urea moeity fully recapitulating hydrogen bonds formed by crystal water in munc18 (red sphere). Syntaxin is identical in ah the structures with the exception of Q119 and T122 sidechains in C1aB/syntaxin, which, in the absence of the crystal water, rotate slightly to satisfy its hydrogen bonds and methyl group interactions.
Figure 6:
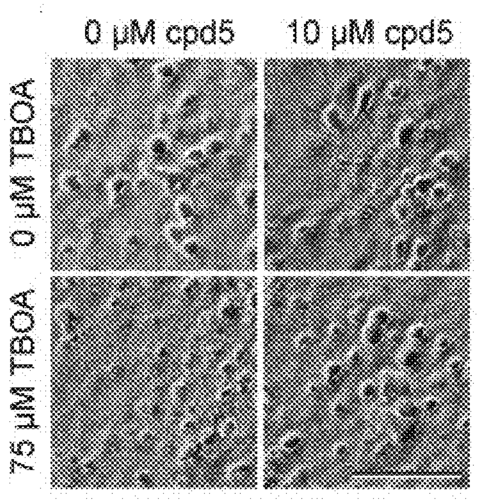
FIG. 6 depicts representative figures of the neuronal culture treated with TBOA, with and without cpd5 pre- and coincubation. Phase-bright cells represent neurons. Scale bar denotes 100 μm.

The loss of munc-18 function blocks neurotransmitter release, causing munc-$18^{-/-}$ animals suffer paralysis and rapid global neurodegeneration after birth (Verhage et al., 2000; Weimer et al., 2003). Although we did not find Cpd5 to be neurotoxic in vitro despite its overlapping binding site with that of munc-18, it remained necessary to evaluate the possibility of Cpd5 inducing irregularities in neuronal excitability and synaptic functions. First, we examined the effects of Cpd5 (10 μM) on the intrinsic electrical properties of layer 5 pyramidal tract neurons in acute slices of mouse cerebral cortex. We were unable to detect any changes in membrane potential (FIG. 5A), input resistance (FIG. 5B), action potential threshold, width, and firing rate (FIG. 5C-G), or F1CN channel-mediated ($I_h$) sag currents (FIG. 5H, I) in neurons treated with Cpd5 when compared to vehicle. We then measured excitatory synaptic potentials evoked in cortical layer 2/3 projection neurons by local electrical stimulation in acute slices. No significant differences were detected in the threshold, amplitude or duration of synaptic potentials evoked in these cells during the application of Cpd5 (10 μM) (FIG. 6A-C). These results demonstrate that at the therapeutic concentration of 10 μM, Cpd5 does not appear to have any measurable action on intrinsic or synaptic properties, potentially ruling out off-target effects of the compound.

All animal protocols described here and below were approved by the Institutional Animal Care and Use Committee of the University of Pittsburgh School of Medicine. Cortical neurons were prepared from embryonic day 16-17 rats of either sex. Pregnant donor rats (Charles River Laboratories) were killed by gradual $CO_2$ inhalation, an American Veterinary Medical Association approved protocol (Leary et al., 2013). Cortices were dissociated with trypsin, and plated at 670,000 cells per well on poly-L-ornithine glass coverslips in six-well plates. Non-neuronal cell proliferation was inhibited with 1-2 μM cytosine arabinoside at 15 days in vitro (DIV). All cortical culture experiments shown here were performed on 18-25 DIV cultures.

DL-threo-β-benzyloxaspartate (TBOA; Tocris Bioscience) excitotoxicity assays were performed on cortical culture coverslips transferred into 24-well plates containing 10 mM HEPES, 0.01% bovine serum albumin (BSA)-supplemented MEM without phenol red (MHB). On each individual plate, coverslips were treated with vehicle control or 75 μM TBOA in wells that had been preincubated for 1 hr with either 10 μM of the indicated treatment or vehicle at 37° C., 5% $CO_2$ for 24 hr. Following this exposure, external medium was collected for LDH colorimetric measurements using a toxicity kit (Sigma-Aldrich), as previously described 12. Each experiment contained three replicates of four conditions (with/without TBOA, with/without treatment). Relative toxicity was quantified as the LDH ratio of TBOA-treated over vehicle control values within each experiment. For visualization of the cell cultures, coverslips were imaged at 20× using a QCapture camera system.

Intracellular $Ca^{2+}$ measurements were performed on the same cortical culture preparations as above, but with 20 DIV cells plated on MatTek glass-bottom 35 mm culture dishes. At this developmental stage, neurons robustly express both GluN2A and GluN2B subunits of the NMDA receptor. Neurons were incubated with the fluorescent $Ca^{2+}$ indicator Fura-2 AM ester (5 μM; Invitrogen) with 0.02% Pluronic F-127 (Invitrogen) for 1 h at 37° C. Culture dishes were then mounted on an inverted microscope stage (Olympus) and continuously perfused with a 10 mM HEPES-buffered normal salt solution. Perfusion rate (5 ml/min) was controlled with a gravity flow and a rapid-switching local perfusion system (Warner Instruments). Firmly attached refractile cells were identified as regions of interest (ROIs; 4 coverslips, ~40 cells/coverslip). A ratio of fluorescence emission (F) at 510 nm in response to excitations at 340 and 380 nm was acquired at 1 Hz (Fambda DG-4 and 10-B SmartShutter, Sutter Instruments) via camera (ORCAER, Hamamatsu) and saved to a computer using HCImage (Hamamatsu). Baseline $Ca^{2+}$ signals were recorded for 2 min before the first application of NMDA (30 μM plus 10 μM glycine) with or without 10 μM cpd5 (Cat #MolPort-009-741-732, Molport). The second exposure to NMDA is given 4 minutes later. Peak increases in intracellular calcium concentration were measured by calculating F/Fo (F, peak fluorescence; Fo, average signal across 2 min baseline period). The area under the response for the first 15 min of NMDA application was also calculated.

Peptide spot array and far-Western assay. Peptide spot arrays (15 mers) spanning the proximal C-terminus residues 451-540 of rat Kv2.1 were constructed using the Spots-synthesis method. Standard 9-fluorenylmethoxy carbonyl (Fmoc) chemistry was used to synthesize the peptides and spot them onto nitrocellulose membranes prederivatized with a polyethylene glycerol spacer (Intavis). Fmoc protected and activated amino acids were spotted in quadruplicates on 20-30 arrays on 75 by 25 mm membranes using an Intavis MultiPep robot. The nitrocellulose membrane containing the immobilized peptides were rehydrated in Tris-buffered 0.1% Tween 20 (TBST) for 10 min, and then blocked for 1 h at room temperature (RT) with gentle shaking in TBST containing 5% (w/v) nonfat dry milk and then incubated with enriched STX1A protein containing the indicated concentrations of cpd5 for 1 h at RT with gentle shaking. Next, the membrane was incubated in primary antibody for syntaxin 1A (Millipore, catalog #AB5820-50UL, RRID:AB_2216165) for 2 h at RT with gentle shaking, followed by washing with TBST. Finally, the membrane was incubated in secondary antibody (goat anti-rabbit DyLight 800, catalog #355571, Thermo Fisher Scientific) for 45 min, washed for 3 times 5 min in TBST, and visualized by infrared fluorescence (Li-Cor). Similar procedures were followed for the alanine scan study with 9-mers.

Cortical culture electrophysiology. Whole-cell patch-clamp experiments were performed on rat cortical culture neurons prepared as described in the LDH toxicity experiments. The TBOA treatment was reduced in severity in this experiment to limit extensive cell injury that would prevent adequate patch clamp recordings. Prior to recording, coverslips were treated with 50 μM TBOA in MHB for 2 hr. The treatment was terminated with 3×MHB washes and transferring the coverslip to a separate well containing MHB to rest for 2 hr prior to electrophysiology recordings and to allow for the expression of enhanced currents. For cpd5-treated groups, cells were pre-incubated for 1 hr in 10 μM cpd5 prior to the addition of TBOA. Cpd5 was also present during the TBOA and the post-TBOA incubation phases.

Recordings were carried out using 1.5 mm diameter borosilicate glass electrodes (Sutter Instruments) made from a horizontal pipette puller at 5-7 MΩ. The internal solution contains (in mM): 100 K-gluconate, 10 KCl, 1 $MgCl_2$, 1 $CaCl_2$, 10 HEPES, 11 EGTA, 2.2 ATP, 0.33 GTP. The internal solution was further adjusted to pH 7.2 and to 280 mOsm with the addition of sucrose. The pH adjusted (7.2) external solution was composed of the following (in mM): 115 NaCl, 2.5 KCl, 2.0 MgCl2, 10 HEPES, 10 D-glucose, and 0.25 μM TTX. Once whole-cell configuration has been achieved, delayed rectifier currents were evoked with 185 ms voltage steps from a holding potential of −80 mV to +80 mV in +10 mV increments. Recordings were filtered at 2 kHz and digitized at 10 kHz (Digidata 1440A, Molecular Devices). Series resistance was compensated at 80% for all recordings. Analysis of current density was carried out at the +30 mV voltage step, taking the mean value of the steadystate current between 150 and 175 ms over the cell capacitance. Normality of the data was confirmed via Shapiro-Wilk test.

Stereotaxic injections for electrophysiology. Male or female ICR mice P21-30 (Jackson Laboratory) were anesthetized with 3% isoflurane (1.5% maintenance) and placed on the stereotaxic frame (Kopf). Core body temperature was maintained at ~37° C. with a heating pad and eyes were protected with ophthalmic ointment. Lidocaine (1%) was injected under the scalp and an incision was made into the skin at the midline to expose the skull. To retrogradely label corticocallosal neurons and corticocollicular neurons in the auditory cortex, the contralateral auditory cortex (PLV −4, +4, +1 mm bregma) and the ipsilateral inferior colliculus (PLV −1, +1, −0.75 mm lambda) respectively were injected with retrograde tracer beads (Lumafluor) through a small craniotomy. A volume of ~0.12 μl fluorospheres was pressure injected (25 psi, 10 ms duration) from capillary pipettes (Drummond Scientific) with a Picospritzer (Parker-Hannifin). After injection, the pipette was held in the brain for 2 min before slowly withdrawing. The scalp of the mouse was closed with cyanoacrylate adhesive. Mice were injected with the non-steroidal anti-inflammatory drug carprofen at 5 mg/kg (Henry Schein Animal Health) for 24 hours prior to and 48 hours after surgery. Mice were monitored for signs of postoperative stress and pain.

Slice electrophysiology. Slice electrophysiology experiments were performed in mice at least 2 days after fluorospheres injections. Following anesthesia with isoflurane, mice were immediately decapitated. Brains were rapidly removed and coronal slices (300 μm) containing the auditory cortex were prepared in a cutting solution at 1° C. using a Vibratome (VT1200 S; Leica). For evoked EPSC recordings, the cutting solution, pH 7.4, ~300 mOsm, contained the following (in mM): 2.5 KCl, 1.25 $NaH_2PO_4$, 25 $NaHCO_3$, 0.5 $CaCl_2$, 7 $MgCl_2$, 7 Glucose, 205 sucrose, 1.3 ascorbic acid, and 3 sodium pyruvate (bubbled with 95% $O_2$/5% $CO_2$). For evaluation of corticocollicular neuron electrical properties, the cutting solution, pH ~7.4, contained the following (in mM): 135 NMDG, 1 KCl, 1.2 $KH_2PO_4$, 1.5 $MgCl_2$, 1.5 CaCl2, 20 $NaHCO_3$, 10 D-Glucose. The slices were then transferred and incubated at 34° C. for 30 min (bubbled with 95% $O_2$/5% $CO_2$) prior to recording. The incubating and recording solution contained the following (in mM): 125 NaCl, 2.5 KCl, 1.25 $NaH_2PO_4$, 25 $NaHCO_3$, 2 $CaCl_2$, 1 $MgCl_2$, 10 D-Glucose, 1.3 ascorbic acid, and 3 sodium pyruvate (bubbled with 95% $O_2$/5% $CO_2$). Slices were stored at room temperature until the time of recording. The flow rate of the ACSF was ~1.5 ml/min, and its temperature was maintained at 34° C. using an in-line heating system (Warner). Both slice electrophysiology experiments were carried out using MultiClamp-700B amplifier equipped with Digidata-1440A A/D converter and Clampex (Molecular Devices). Data were sampled at 10 kHz and Bessel filtered at 4 kHz. Pipette capacitance was compensated and series resistance for recordings was lower than 15 MΩ and measured throughout the experiments. Recordings were excluded from further analysis if the series resistance changed by more than 15% compared to the baseline period.

To evoke AMPAR EPSCs, auditory cortex layer 2/3 neurons were stimulated locally with an Isoflex stimulator (AMPI), through a glass theta electrode containing ACSF, by a single 0.15 ms duration electrical pulse every 30 sec. AMPAR EPSCs were recorded in voltage clamp mode at −70 mV (peak values were averaged over a 0.3 ms time window).

All data for intrinsic properties were acquired and analyzed within the Ephus software package. Series resistance was determined in voltage-clamp mode (command potential set at −70 mV) by giving a −5 mV voltage step. Series resistance was determined by dividing the −5 mV voltage step by the peak current value generated immediately after the step in the command potential $R_{input}$ was calculated in voltage-clamp mode (command potential set to −70 mV) by giving a −5 mV step, which resulted in transient current responses. The difference between baseline and steady-state hyperpolarized current (ΔI) was used to calculate $R_{input}$ using the following formula: $R_{input}$=−5 mV/ΔI−$R_{series}$. The average resting membrane potential ($V_m$) was calculated by holding the neuron in voltage-follower mode (current clamp, at I=0) ~2 minutes after breaking in and averaging the membrane potential over the next 30 sec. Subthreshold and suprathreshold membrane responses in current clamp were elicited by injecting −200 to +400 pA in 50 pA increments (baseline Vm was maintained at −70 mV, by injecting the required current, if necessary). Sag was measured during the −200 pA current injection, using the formula, SAG=($V_{min}$−$V_{steady\text{-}state}$)/$V_{steady\text{-}state}$. The first resulting action potential (AP) at rheobase was analyzed for AP width. AP width was calculated as the full-width at the half-maximum amplitude of the AP.

Both slice electrophysiology experiments utilized borosilicate pipettes (World Precision Instruments) pulled into patch electrodes with 2.5-6 MΩ resistance (Sutter Instruments) and filled with a potassium-based intracellular solution, which was composed of the following (in mM): 128 K-gluconate, 10 HEPES, 4 $MgCl_2$, 4 $Na_2ATP$, 0.3 Tris-GTP, 10 Tris phosphocreatine, 1 EGTA, and 3 sodium ascorbate (pH=7.25, 295 mOsm). Normality of the data collected was confirmed via Shapiro-Wilk test.

Western Blot. Co-immunoprecipitation of munc18 and syntaxin was carried out using PEI transfection of HEK293 cells (American Type Culture Collection) plated and maintained in DMEM medium with 10% FBS and penicillin/streptomycin. 24 hr prior to transfection, HEK293 cells are plated onto 150 mm petri dishes from confluent T75 flasks at the ratio of 2/3 flask per plate. 24 hr after plating, PEI transfection was carried out by mixing 25% munc18 (OriGene RC204873), 25% syntaxin 1A (gift from Raymond A Frizzell, Children's Hospital of Pittsburgh), and 50% pcDNA3 (Invitrogen) plasmids (28 pg total plasmids with 500 μl medium without penicillin/streptomycin, and 110 μl PEI at 1 mg/ml). The PEI was lastly added to the mixture drop-wise to avoid clumping of the DNA precipitates. This transfection reagent was allowed to incubate in room temperature for at least 5 min. The HEK293 medium was replaced with medium without penicillin/streptomycin prior to the addition of the transfection mixture. At 24 hr after transfection, the transfection medium was replaced with regular medium containing either cpd5 or DMSO. The cells were lysed and protein was harvested 24 hr after cpd5/DMSO treatment using 200 μl NP40 buffer (Invitrogen) containing phenylmethylsulfonyl fluoride (PMSF, Sigma-Aldrich) and protease inhibitor cocktail (¼ tablet, cOmplete Mini, EDTA-free, Sigma-Aldrich). The resulting HEK293 sample was immunoprecipitated using mouse anti-syntaxin 1A antibody (abeam). The western blot was probed using the Biogen system with the same syntaxin 1A antibody and mouse anti-Flag (Sigma-Aldrich) used for the detection of munc18. Quantification of protein pulldown was normalized to the syntaxin signal before comparisons. SDS-PAGE in this study are run in 10% acrylamide. Small variations in band separation are caused by the semi-wet transfer method.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A method of treating a neurological condition in a subject in need thereof, comprising administering to the subject a pharmaceutical composition comprising a compound of Formula (I):

[Formula (1)]

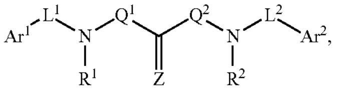

or a pharmaceutically acceptable salt thereof, wherein:

Z is O;

$R^1$ and $R^2$ are each hydrogen;

$Q^1$ and $Q^2$ are each absent; or $Q^1$ is absent and $Q^2$ is a group having the formula —$(CR^{q2}R^{q2'})$—, wherein $R^{q2}$ is hydrogen and $R^{q2'}$ is hydrogen, OH, or $C_{1-6}$alkyl;

$L^1$ is —$(CR^4R^{4'})_n$-, wherein:

n is 0, 1, 2, 3, 4, 5, 6, 7, or 8;

$R^4$ is in each case independently hydrogen or $C_{1-8}$alkyl;

$R^{4'}$ is in each case independently hydrogen or $C_{1-8}$alkyl;

$Ar^1$ has the formula:

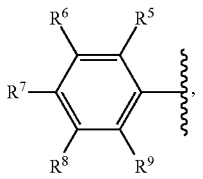

wherein, $R^5$ is F, Cl, Br, $R^{5a}$, or $OR^{5a}$, wherein $R^{5a}$ is hydrogen or $C_{1-8}$alkyl;

$R^6$ is F, Cl, Br, $R^{7a}$, or $OR^{6a}$, wherein $R^{6a}$ is hydrogen or $C_{1-8}$alkyl;

$R^7$ is F, Cl, Br, $R^{7a}$, or $OR^{7a}$, wherein $R^{7a}$ is hydrogen or $C_{1-8}$alkyl;

$R^8$ is F, Cl, Br, $R^{8a}$, or $OR^{8a}$, wherein $R^{8a}$ is hydrogen or $C_{1-8}$alkyl;

$R^9$ is F, Cl, Br, $R^{9a}$, or $OR^{9a}$, wherein $R^{9a}$ is hydrogen or $C_{1-8}$alkyl;

wherein any two or more of $R^5$, $R^6$, $R^7$, $R^8$, and $R^9$ may together form a ring;

$L^2$ is absent, a group having the formula —$(CR^{10*}R^{10'})_{n'}$-, or —$(CH_2)_p$-Cy-$(CH_2)_o$—, wherein:

p is 0, 1, 2, 3, 4, 5, or 6;

o is 0, 1, 2, 3, 4, 5, or 6;

Cy is an optionally substituted aryl group; an optionally substituted $C_{1-8}$heteroaryl group; an optionally substituted $C_{3-8}$cycloalkyl group; or an optionally substituted $C_{1-8}$heterocyclyl group;

n' is from 0-8;

$R^{10*}$ is in each case independently hydrogen or $C_{1-8}$alkyl;

$R^{10'}$ is in each case independently hydrogen or $C_{1-8}$alkyl; and $Ar^2$ has the formula:

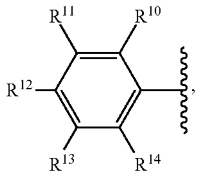

wherein $R^{10}$ is F, Cl, Br, or $R^{10a}$, wherein $R^{10a}$ is in each case independently selected from hydrogen, $C_{1-13}$alkyl, $C_{1-8}$heteroaryl, or $C_{1-8}$heterocyclyl;

$R^{11}$ is F, Cl, Br, or $R^{11a}$, wherein $R^{11a}$ is in each case independently selected from hydrogen, $C_{1-13}$alkyl, $C_{1-8}$heteroaryl, or $C_{1-8}$heterocyclyl;

$R^{12}$ is F, Cl, Br, or $R^{12a}$ wherein $R^{12a}$ is in each case independently selected from hydrogen, $C_{1-13}$alkyl, $C_{1-8}$heteroaryl, or $C_{1-8}$heterocyclyl;

$R^{13}$ is F, Cl, Br, or $R^{13a}$, wherein $R^{13a}$ is in each case independently selected from hydrogen, $C_{1-13}$alkyl, $C_{1-8}$heteroaryl, or $C_{1-8}$heterocyclyl;

$R^{14}$ is F, Cl, Br, or $R^{14a}$, wherein $R^{14a}$ is in each case independently selected from hydrogen, $C_{1-13}$alkyl, $C_{1-8}$heteroaryl, or $C_{1-8}$heterocyclyl;

wherein any two or more of $R^{10}$, $R^{11}$, $R^{12}$, $R^{13}$, and $R^{14}$ may together form a ring, wherein one of $R^{10}$, $R^{11}$, $R^{12}$, $R^{13}$, or $R^{14}$ is a $C_{1-8}$heteroaryl having the formula:

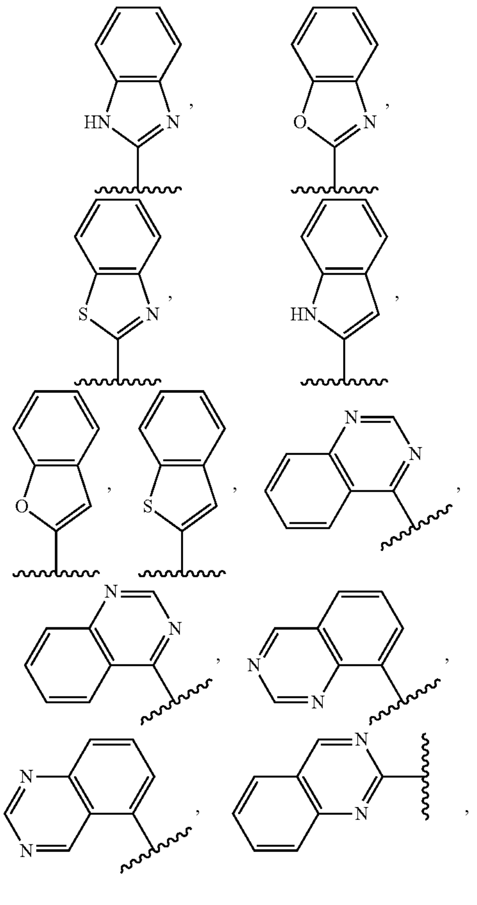

-continued

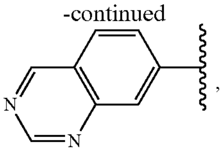,

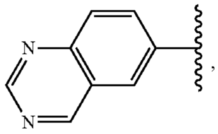, 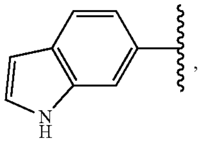,

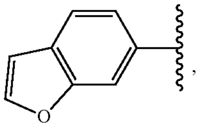, 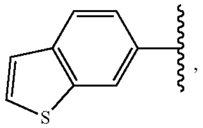,

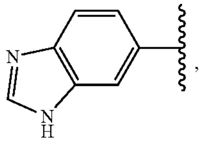, 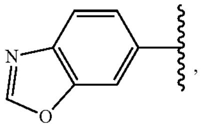,

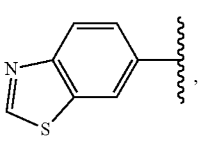, 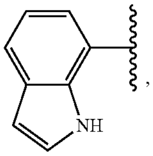, 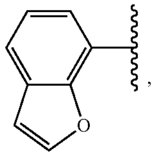,

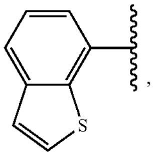, 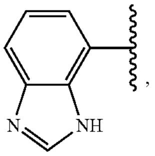, 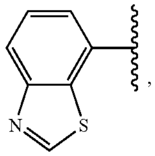,

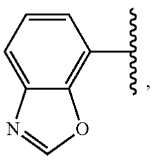, 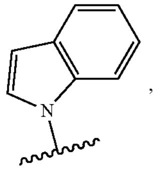, or 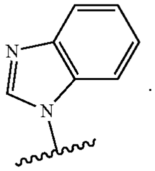.

2. The method of claim 1, wherein $L^2$ has the formula:

$$-(CH_2)_p\text{-Cy-}(CH_2)_o-,$$

p is 0, 1, or 2; o is 0, 1, or 2; and Cy is optionally substituted $C_{1-8}$heterocyclyl group.

3. The method of claim 1, wherein $Q^2$ is absent or a group having the formula $(CR^{q2}R^{q2'})$, wherein $R^{q2}$ is hydrogen and $R^{q2'}$ is OH.

4. The method of claim 1, wherein $L^2$ is absent.

5. The method of claim 1, wherein $R^{10}$ is $R^{10a}$ wherein $R^{10a}$ is hydrogen or $C_{1-8}$heteroaryl;

$R^{11}$ is $R^{11a}$ wherein $R^{11a}$ is hydrogen or $C_{1-8}$heteroaryl;

$R^{12}$ is $R^{12a}$, or $OR^{12a}$, wherein $R^{12a}$ is hydrogen or $C_{1-8}$heteroaryl;

$R^{13}$ is $R^{13a}$ wherein $R^{13a}$ is hydrogen or $C_{1-8}$heteroaryl;

$R^{14}$ is F, Cl, Br, $R^{14a}$, or $OR^{14a}$, wherein $R^{14a}$ is hydrogen or $C_{1-8}$heteroaryl.

6. The method of claim 1, wherein $Ar^2$ has the formula:

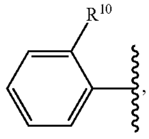, 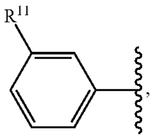, 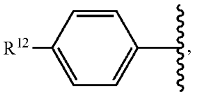,

-continued

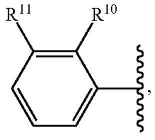, 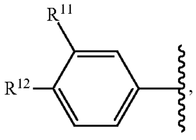, 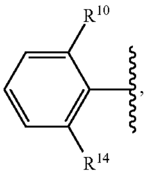,

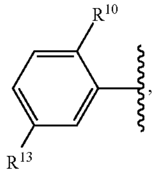, 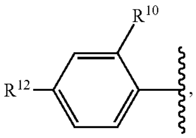, 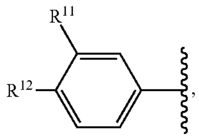,

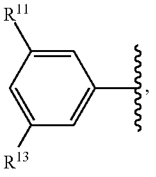, or 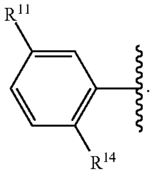.

7. The method of claim 1, wherein $Ar^2$ has the formula:

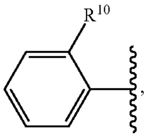, 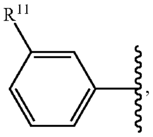, or 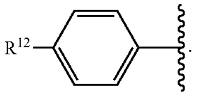.

8. The method of claim 7, wherein one of $R^{10}$, $R^{11}$, and $R^{12}$ is:

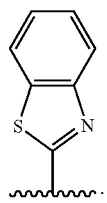.

9. The method of claim 7, wherein the compound has the formula:

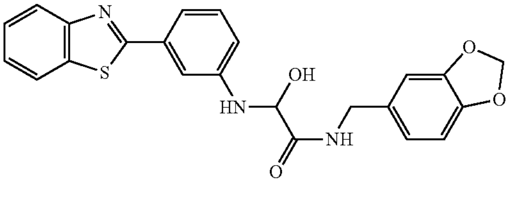 or

-continued

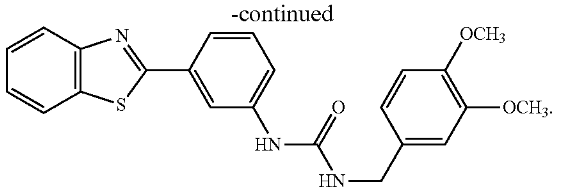

10. The method of claim 1, wherein $L^1$ is $CH_2$.

11. The method of claim 1, wherein $Ar^1$ has the formula:

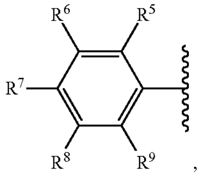

wherein each of $R^5$, $R^8$, and $R^9$ are hydrogen.

12. The method of claim 11, wherein $R^6$ and $R^7$ are $C_{1-4}$alkoxy, and may together for a ring.

13. The method of claim 11, wherein $R^6$ and $R^7$ are each methoxy, or $Ar^1$ has the formula:

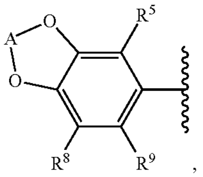

wherein A is $CH_2$ or $CH_2CH_2$.

14. The method according to claim 1, wherein the neurological condition comprises a neurodegenerative disease.

15. The method according to claim 14, wherein the neurodegenerative disease comprises Alzheimer's disease, Parkinson's disease, Huntington's disease, ALS, multiple sclerosis, Lewy body dementia, vascular dementia, progressive supranuclear palsy, corticobasal degeneration, multiple system atrophy or frontotemporal dementia.

16. The method according to claim 1, wherein the neurological disorder comprises a neurological injury.

17. The method according to claim 16, wherein the neurological injury comprises cerebral ischemia, stroke, CNS trauma/injury, traumatic brain injury, or any other condition associated with neuronal damage or neuronal cell death.

* * * * *

UNITED STATES PATENT AND TRADEMARK OFFICE

CERTIFICATE OF CORRECTION

PATENT NO. : 12,226,400 B2
APPLICATION NO. : 17/264982
DATED : February 18, 2025
INVENTOR(S) : Elias Aizenman and Carlos Jaime Camacho It is certified that error appears in the above-identified patent and that said Letters Patent is hereby corrected as shown below:

In the Claims

Column 31, Claim 1, Line 54, reading:
$L^2$ is absent, a group having the formula—$(CR^{10*}R^{10'})n'$-,
Should read:
$L^2$ is absent, a group having the formula—$(CR^{10*}R^{10'})n'$—, Column 35, Claim 12, Line 28, reading:
$C_{1-4}$alkoxy, and may together for a ring.
Should read:
$C_{1-4}$alkoxy, and may together form a ring.

Signed and Sealed this
Twelfth Day of August, 2025

Coke Morgan Stewart
*Acting Director of the United States Patent and Trademark Office*